United States Patent [19]
Guentert et al.

[11] Patent Number: 5,366,122
[45] Date of Patent: Nov. 22, 1994

[54] DISPENSER FOR FLOWABLE MEDIA

[75] Inventors: Bernhard Guentert, Ehingen, Germany; Michael Wolter, Steckborn, Switzerland; Stefan Ritsche; Reinhold Jaeger-Waldau, both of Radolfzell,, Germany; Karl-Heinz Fuchs, Radolfzell, Germany

[73] Assignee: Ing. Erich Pfeiffer GmbH & Co. KG, Germany

[21] Appl. No.: 936,743

[22] Filed: Aug. 27, 1992

[30] Foreign Application Priority Data

Aug. 27, 1992 [DE] Germany ............................ 4128295

[51] Int. Cl.⁵ .................................... B65D 83/06
[52] U.S. Cl. ...................... 222/401; 222/631; 222/636; 239/305; 239/307
[58] Field of Search ............... 222/133, 401, 631, 634, 222/635, 636; 604/24, 58; 239/305, 307

[56] References Cited

U.S. PATENT DOCUMENTS

| | | | |
|---|---|---|---|
| 3,080,095 | 5/1963 | Woroble | 222/89 |
| 3,300,145 | 1/1967 | Marraffino | 239/307 |
| 3,335,961 | 8/1967 | Marraffino | 239/305 |
| 3,764,046 | 9/1973 | Riccio | 222/635 |
| 3,858,659 | 1/1975 | Fukushima | 169/77 |
| 3,906,950 | 9/1975 | Cocozza | 128/266 |
| 4,214,677 | 7/1980 | Bauer et al. | 222/145 |
| 4,811,731 | 3/1989 | Newell et al. | 604/58 X |
| 4,860,740 | 8/1989 | Kirk et al. | 604/58 X |
| 4,989,763 | 2/1991 | Brunet | 222/80 X |

FOREIGN PATENT DOCUMENTS

| | | |
|---|---|---|
| 230968 | 8/1987 | European Pat. Off. . |
| 342741 | 11/1989 | European Pat. Off. . |
| 2176225 | 10/1973 | France . |
| 1482675 | 7/1969 | Germany . |
| 2337220 | 2/1975 | Germany . |
| 9017326 | 12/1990 | Germany . |
| 4027749 | 3/1992 | Germany . |
| WO9007351 | 7/1990 | WIPO . |
| WO9106333 | 5/1991 | WIPO . |

OTHER PUBLICATIONS

JP 63-39656 A., In: Patents Abstracts of Japan, C-512, Jul. 15, 1988, vol. 12, No. 252.

*Primary Examiner*—Andres Kashnikow
*Assistant Examiner*—Joseph A. Kaufman
*Attorney, Agent, or Firm*—Quarles & Brady

[57] ABSTRACT

In a discharge apparatus (1) on a basic body (8) is provided a pneumatic pump (19) and axially adjacent thereto a casing chamber (14) for receiving a magazine (15) for individual doses of a pulverulent or similar medium, whose magazine chamber (30) can be transferred into a discharge position, in which it is connected by one inlet end (46) and one outlet end (47) to a feed path (20) for the pumped air. At remote ends of the basic body (8) are provided pressure handles (5, 6) for the discharge actuation and a handle (7) for indexing or replacing a magazine body (16). Opening devices (50, 51) are used for the automatic opening of the magazine chamber (30) on transfer into the discharge position. This leads to a very reliable operation in the case of compact construction and easy handling.

57 Claims, 11 Drawing Sheets

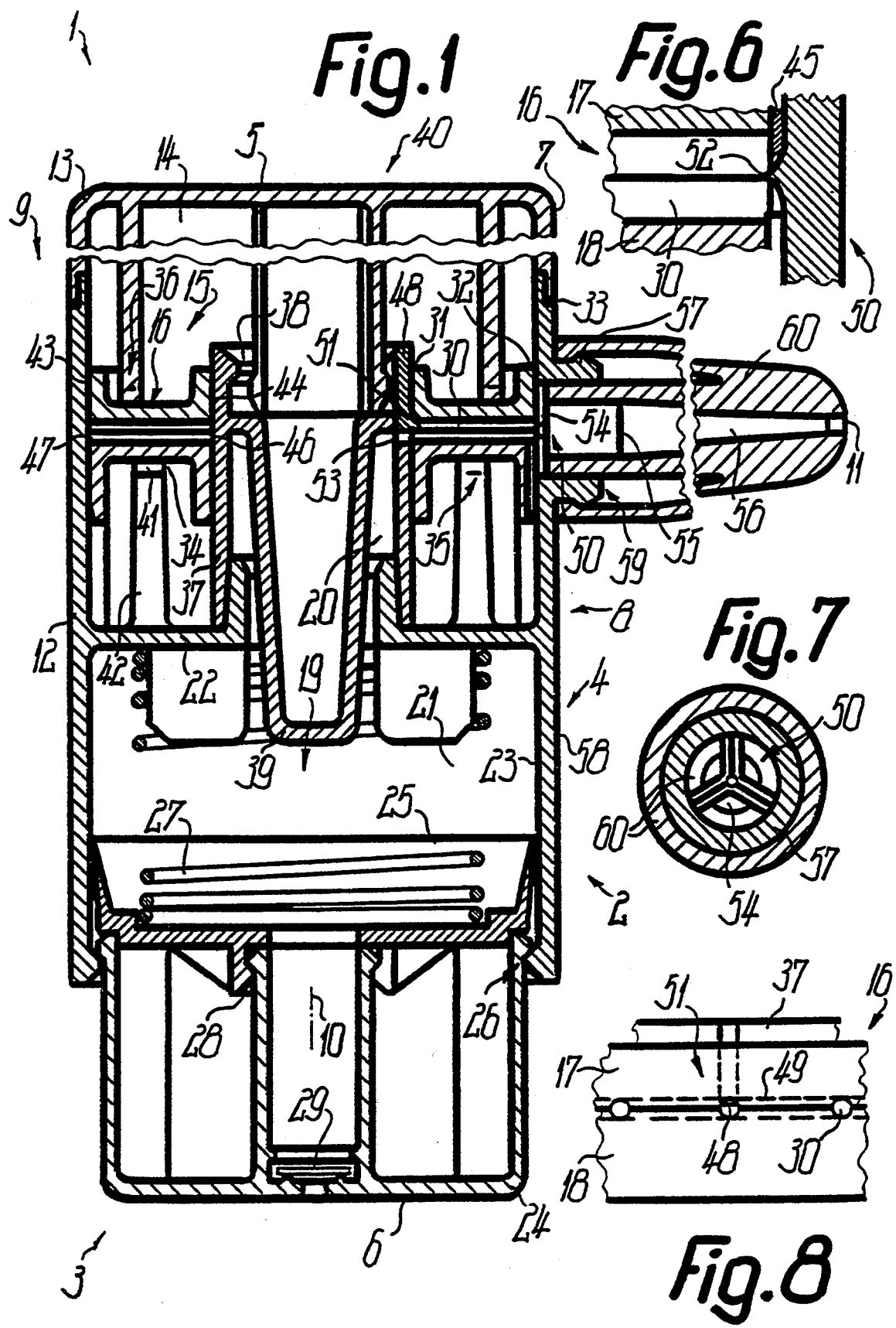

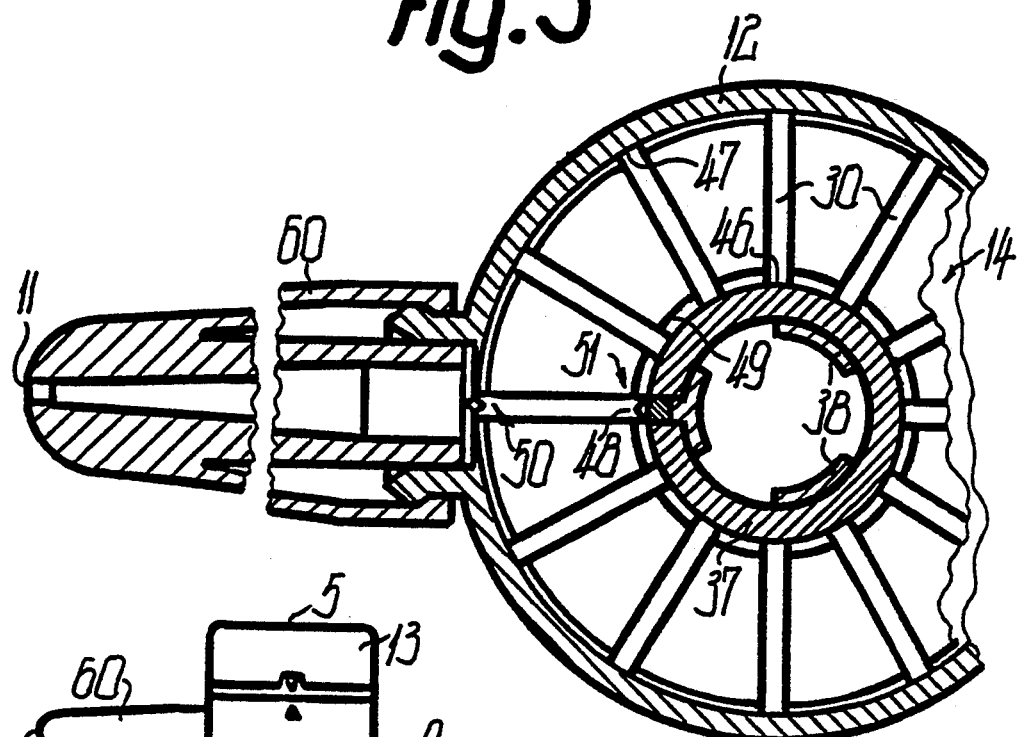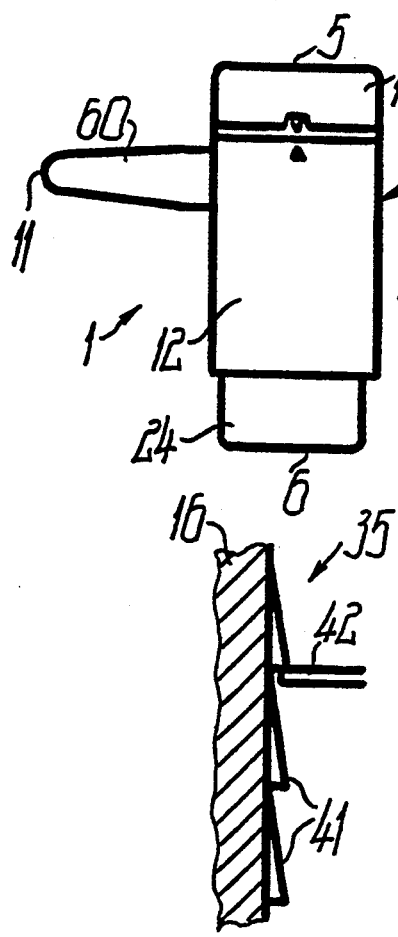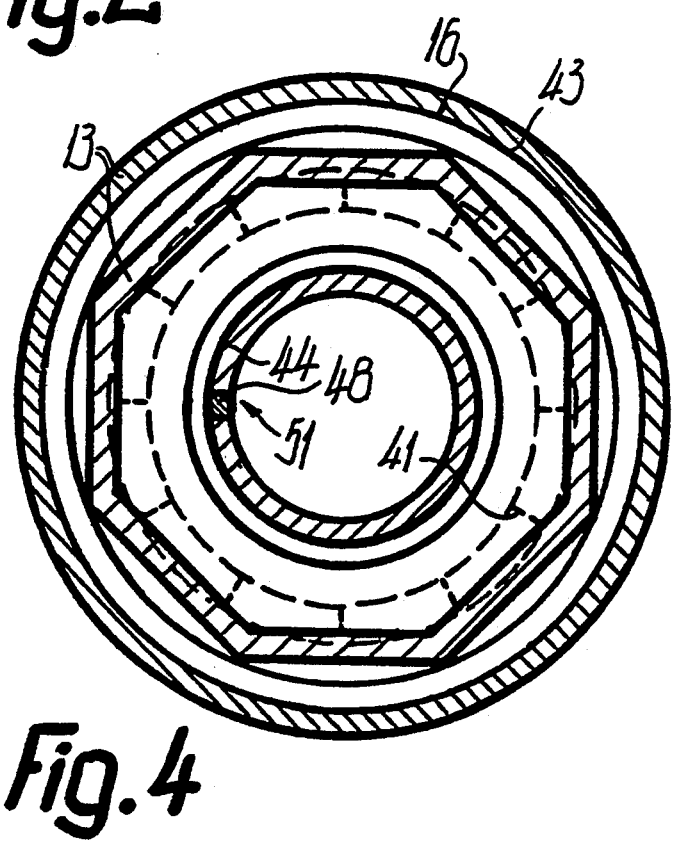

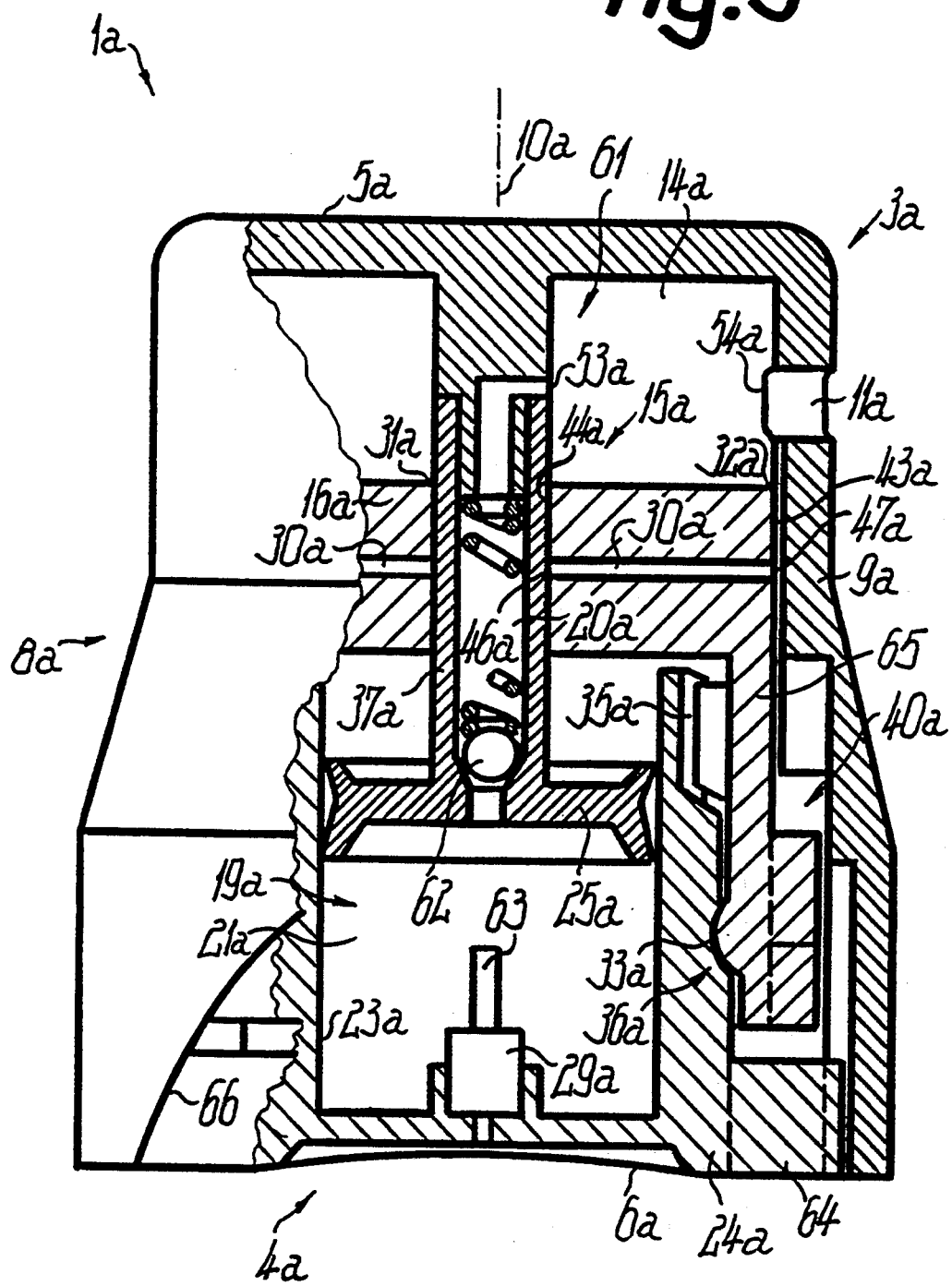

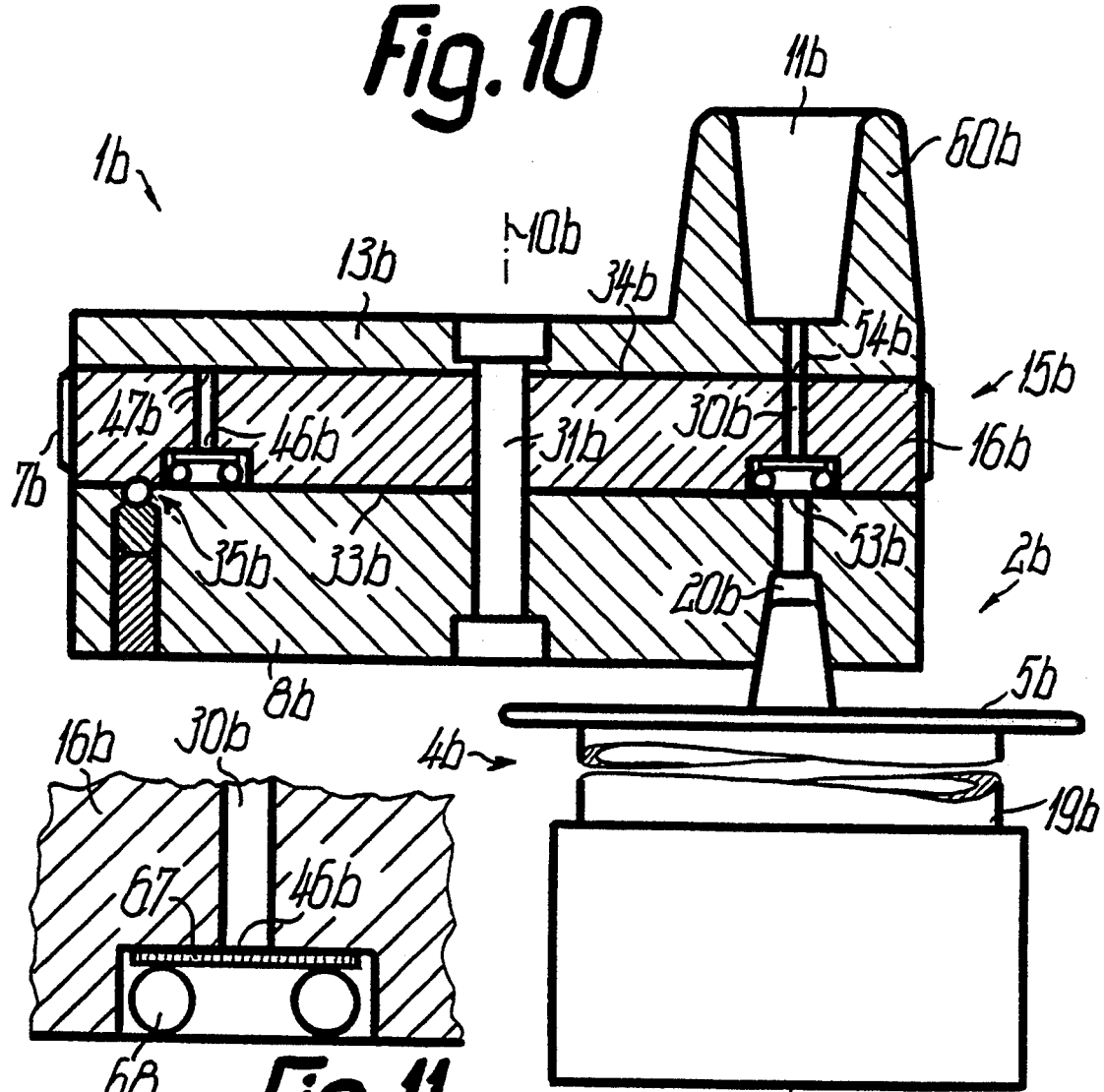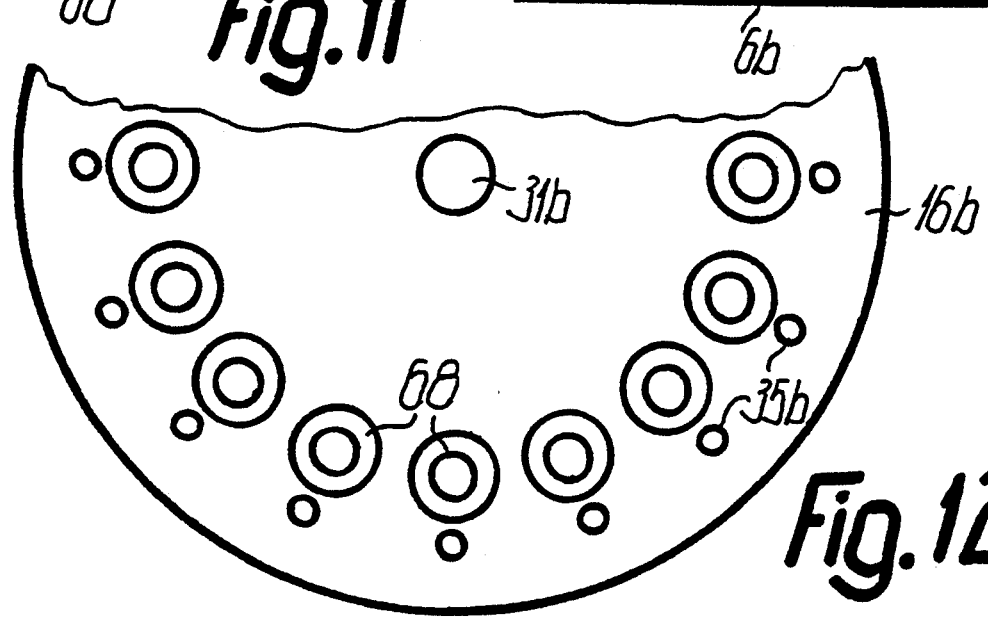

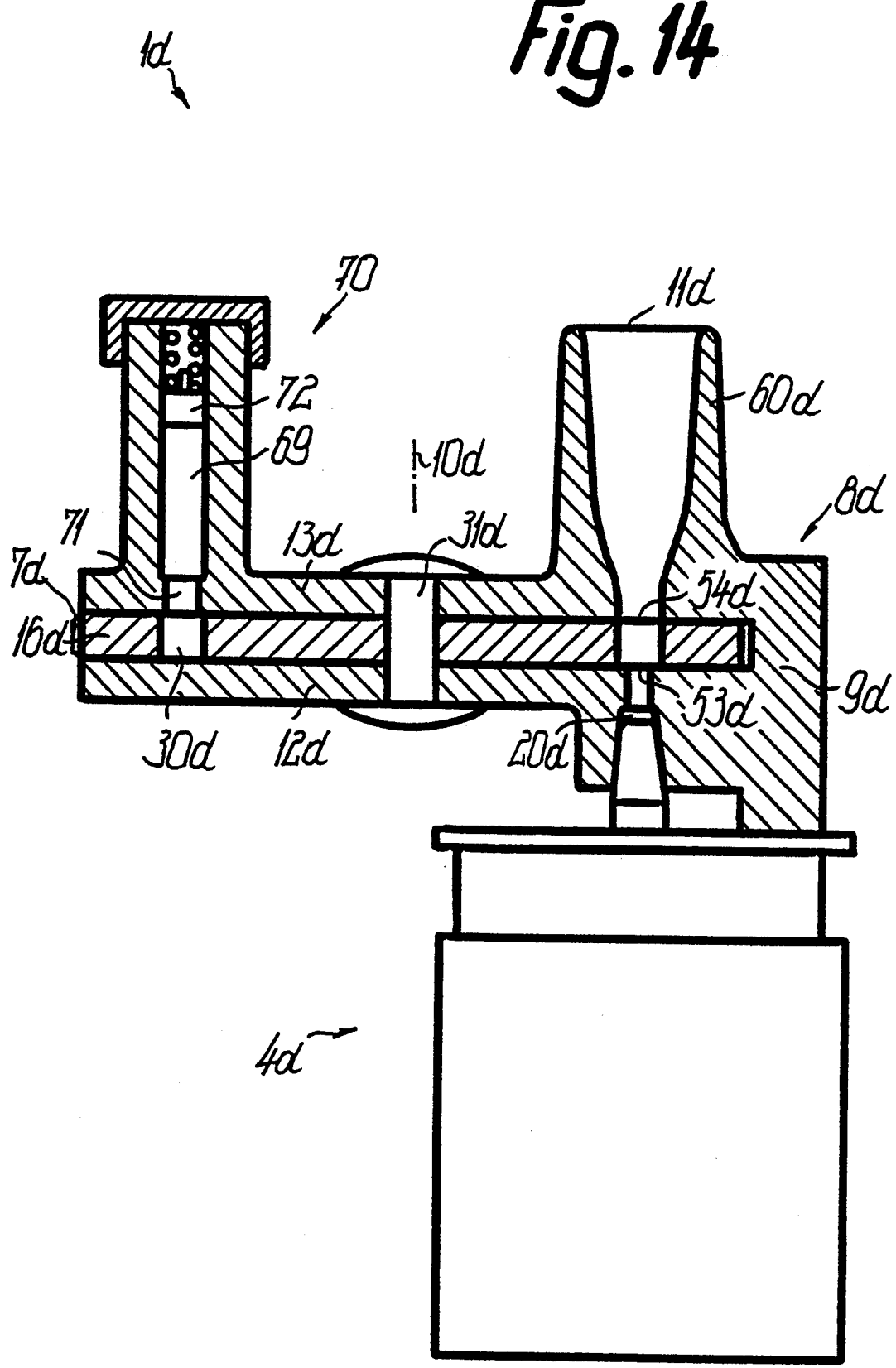

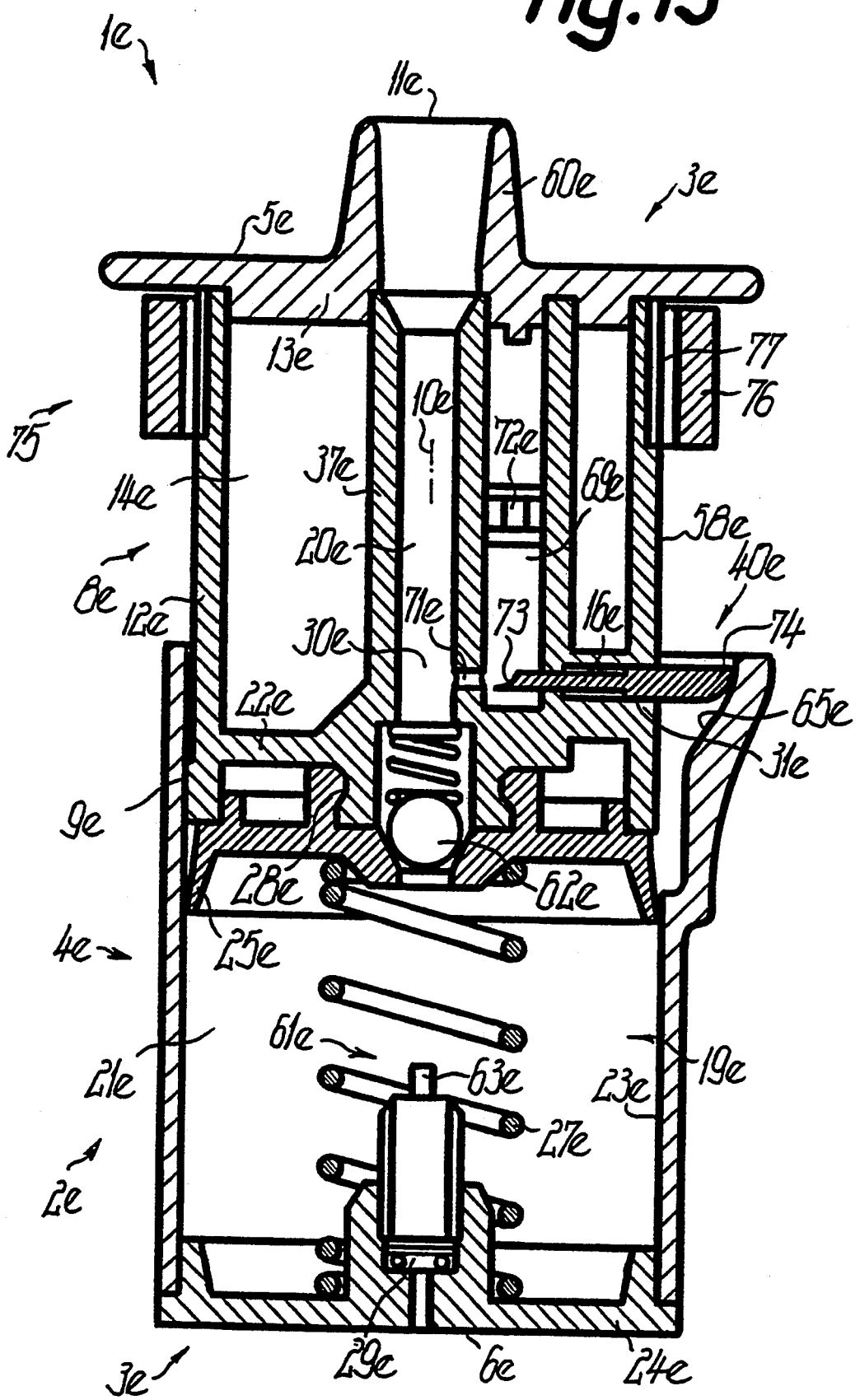

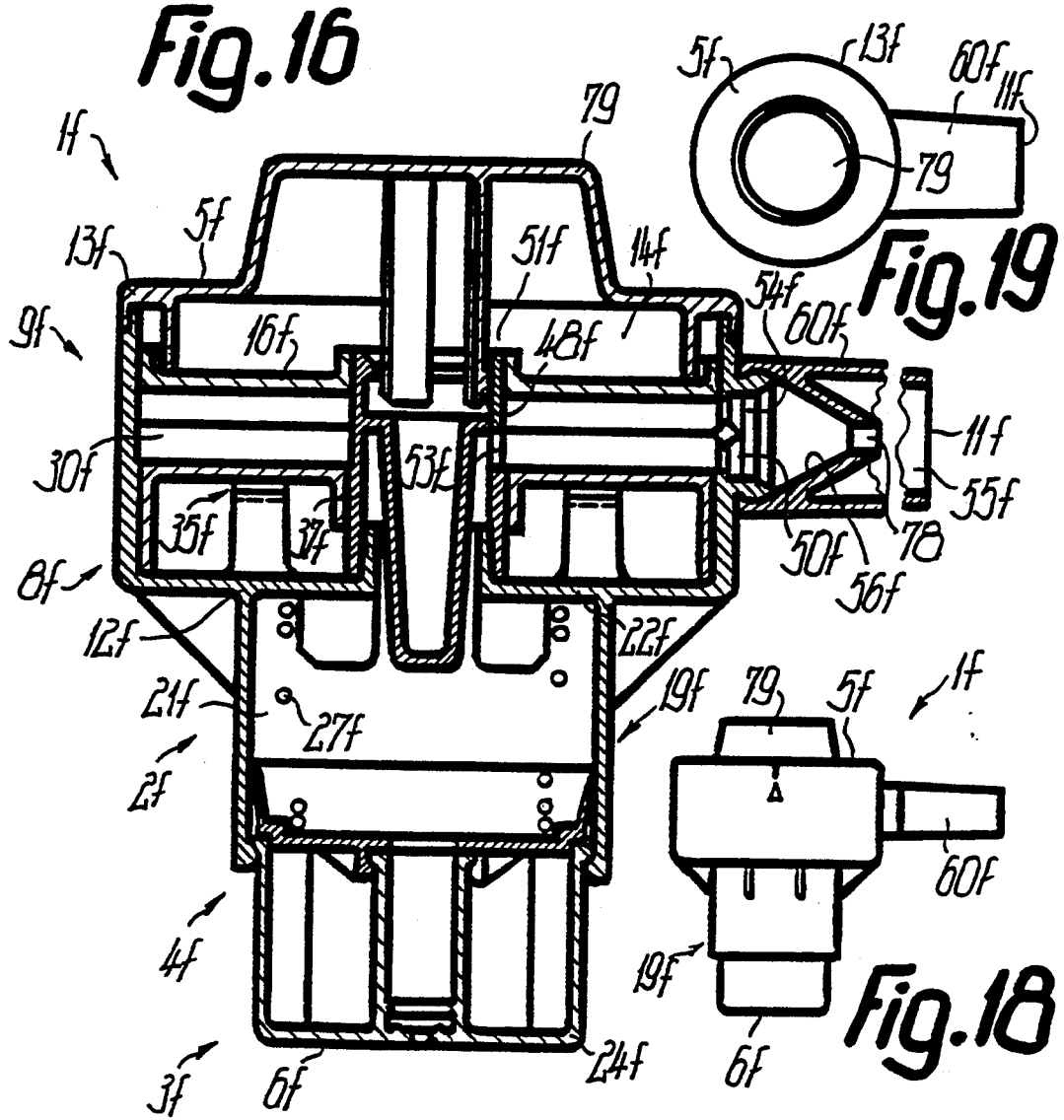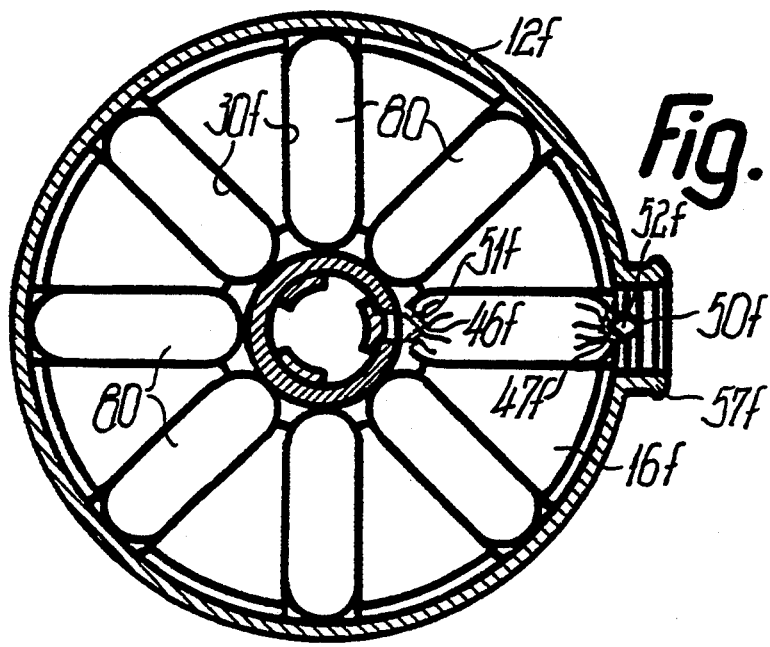

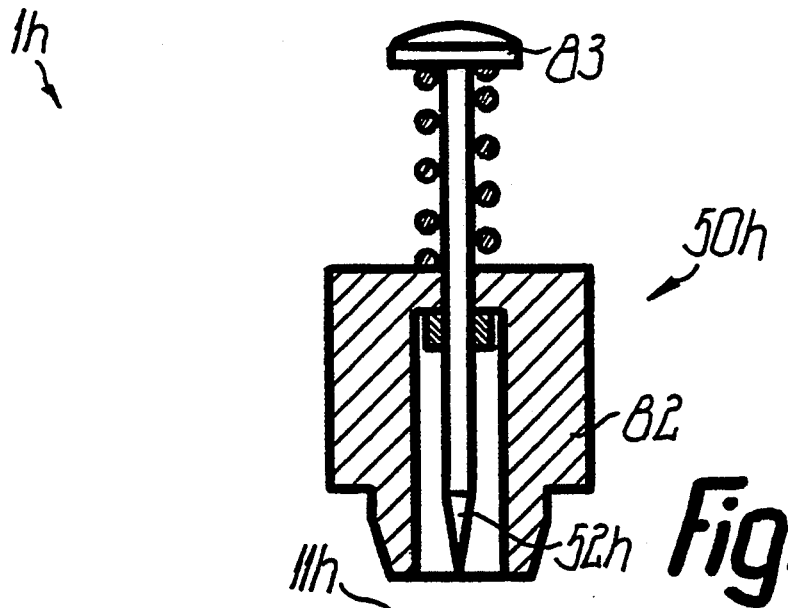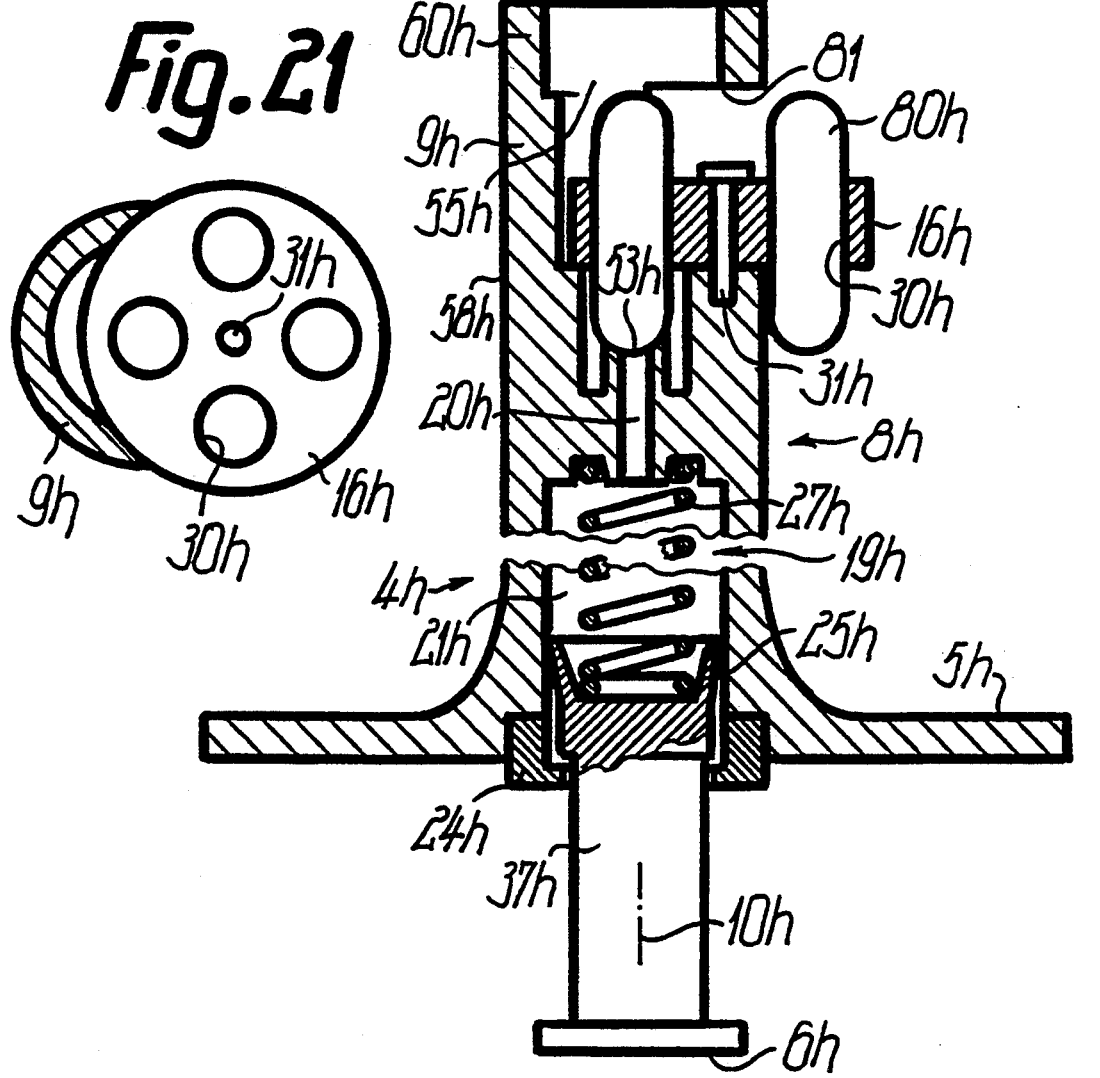

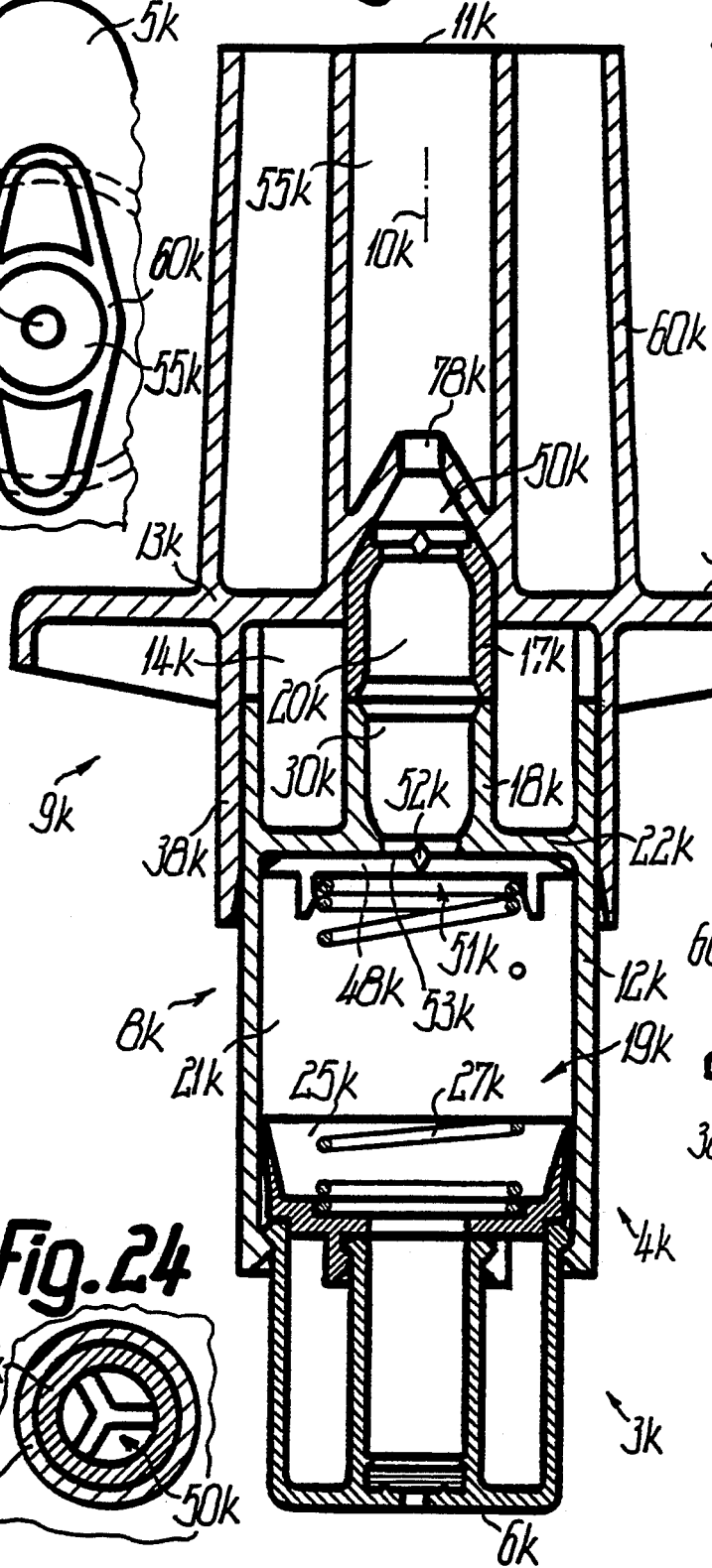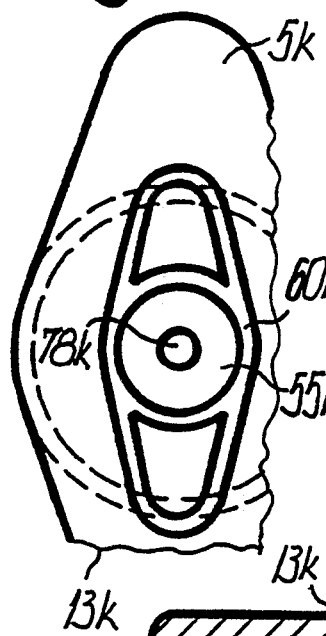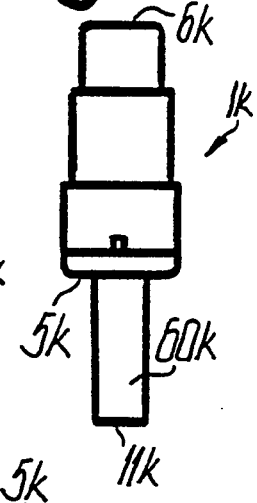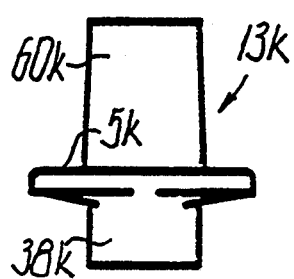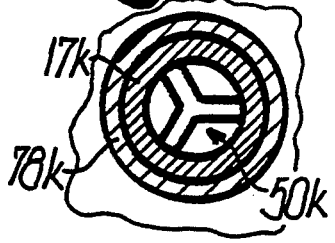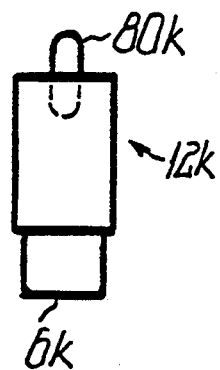

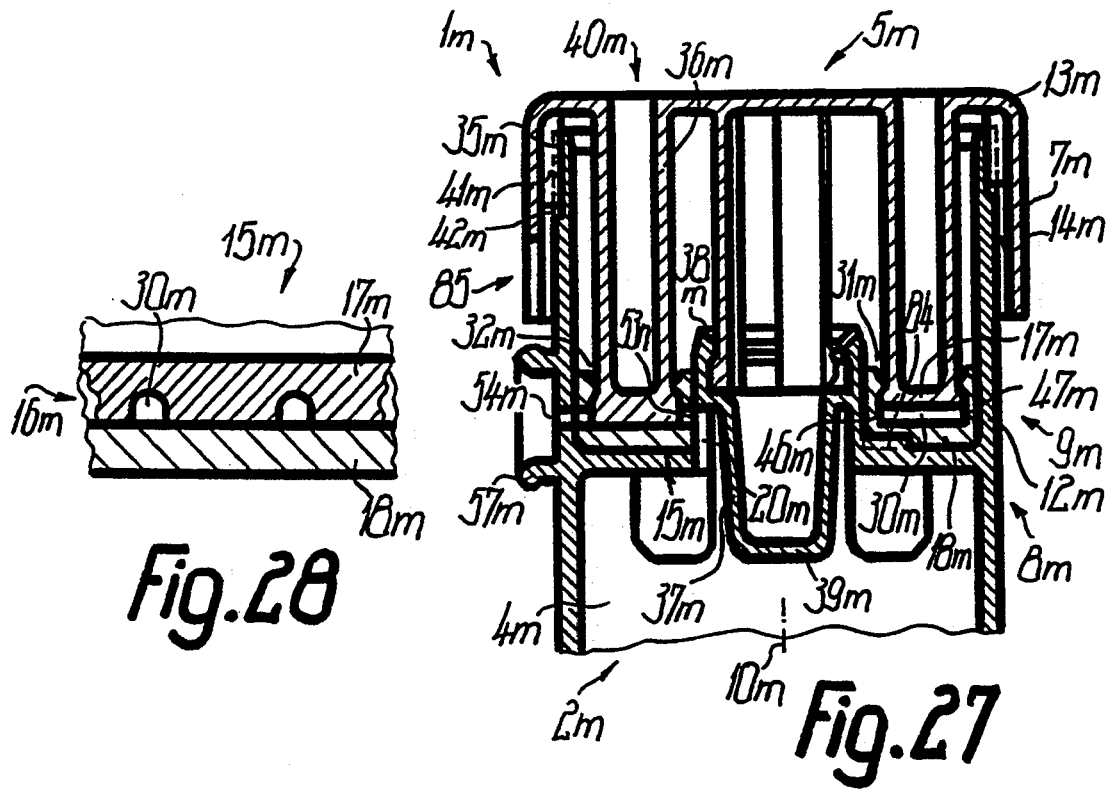
Fig. 28
Fig. 27
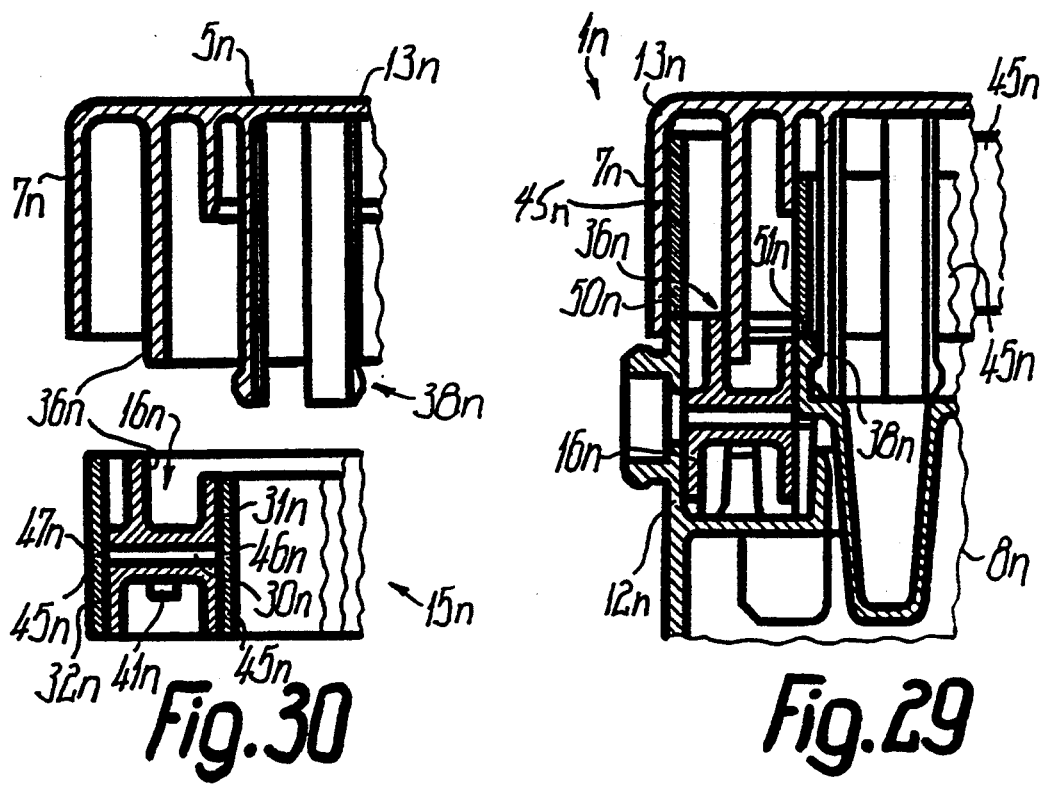
Fig. 30
Fig. 29

DISPENSER FOR FLOWABLE MEDIA

BACKGROUND OF THE INVENTION

The invention relates to a discharge apparatus for media and is in particular suitable for free-flowing or bulk media constituted by fine solid particles, which can be pulverulent, powder-like or flour-like. This medium can be discharged in a whirled up, dry dust flow and/or can be at least partly mixed prior to discharge with a further, e.g. a liquid medium. For discharge purposes a random discharge operation performed by the operator takes place and as a result a discharge conveyor is put into operation in such a way that the medium or medium mixture can be discharged into the open through a discharge opening in the discharge apparatus, so that it can be used in the intended way.

Free-flowing media, e.g. for medical or therapeutic purposes, such as for inhalation, as well as for technical and other purposes are used in such a way that they are discharged in a very uniform, loosened distribution of the substantially homogeneously individualized or separated particles. For this purpose, according to the invention, the medium quantity to be discharged in a discharge process can be brought into a reception position sealed off from further medium supplies and in which the initially compact medium is exposed to a gaseous or some other feed flow through which its particles are separated, accompanied by whirling up and are then transported to the discharge opening.

Instead of producing the feed flow by suction or breathing air or a generator or producer separate from the discharge apparatus, appropriately a generator or producer is structurally combined with the discharge apparatus and the basic body thereof is substantially rigidly connected to the basic body of the discharge apparatus. The generator can e.g. be a propellant gas-filled pressure vessel, which can be put into operation by the manual opening of a valve, or is preferably an air or pneumatic pump, which by the mechanical drive of its pump movement sucks in air, compresses it and delivers it in the direction of the reception chamber.

It is particularly advantageous if the generator is approximately axially parallel, equiaxial and/or axially immediately adjacent to a magazine for the medium, because then in the case of small external dimensions of the discharge apparatus short line paths and high efficiency are ensured. The discharge apparatus can also be constructed for manually freely carried, untethered one-handed operation, in which with at least two facing fingers of the user's hand the feed flow is put into operation and consequently medium is discharged.

OBJECTS OF THE INVENTION

An object of the invention is to provide a discharge apparatus of the aforementioned type, in which disadvantages of known constructions or of the described kind are avoided and which in particular in the case of a simple, compact construction ensures a very finely divided, uniform discharge of individual medium doses.

SUMMARY OF THE INVENTION

The apparatus can have one or more magazine bodies, one or more generators, one or more discharge openings, one or more separately operable discharge actuations or discharge conveyors, one or more separate control mechanisms for indexing the particular magazine body, one or more separate refilling devices for refilling at least one magazine chamber with medium, one or more vibrators for loosening or after-feeding the medium and other means to be described hereinafter, which can be formed on a discharge apparatus in substantially identical or non-identical manner with respect to their construction and/or function.

Appropriately a magazine body is provided with radial and/or axial magazine chambers, which can be elongated in channel-like manner in such a way that they essentially form an intermediate section of the feed path loosely plugged with the medium. This intermediate section is then, in the discharge position of the particular magazine chamber, only connected by one end to a supplying section of the feed path and with the end remote therefrom to a conveying away section of the feed path or directly to the discharge opening, so that the medium contained in the magazine chamber can be ejected. The boundary of the medium chamber can be directly formed by the magazine body or by, a capsule, which is placed in a corresponding magazine receptacle of the magazine body.

In order to be able to move the magazine body between an inoperative position and a discharge position of the particular medium chamber, it can be directly connected in synchronized manner with a handle accessible from the outside or an indexing drive can be provided between such a handle and the magazine body and which e.g. converts an axial movement into a transverse or rotary movement, the indexing of the chamber body taking place in path-dependent manner simultaneously with the operation of the generator and also independently thereof as a result of a separate actuation. For indexing purposes the magazine body can be arranged in a rotary and/or axially displaceable manner, as a function of whether the magazine chambers are located only in a ring, parallel to one another and in succession in the displacement direction, or in several rings which are axially adjacent to one another.

In place of prefilled reception or magazine chambers or in addition thereto, it is also possible to provide a refilling device for the reception chamber or for the at least one magazine chamber. This refilling device can be a rotary slide valve with one or mope magazine chambers, which for refilling purposes are made to coincide with a passage opening of a storage magazine and from there can be made to coincide with following sections of the feed path, so that through the filling of one or more storage magazines which have become empty, the apparatus can always be made ready to operate again and for this purpose only suitable refilling packs are necessary.

A refilling slide valve for the reception chamber can also be linearly movable and arranged in such a way that through a transverse movement it is moved through a storage shaft and thereby forces medium through one or more wall openings of said shaft into the reception chamber. By appropriate spring-loaded bounding of the storage chamber receiving the medium or by following vibrating movements, it is always possible to ensure that in the vicinity of the transport end of the valve in uninterrupted manner medium is made available in the storage shaft. However, it is always possible to construct the magazine body in such a way that it only receives a single medium dose to be discharged and which has to be reintroduced anew, following its opening, for each apparatus discharge use.

It is particularly advantageous if the magazine body, in the operating state, is completely surrounded with respect to the outside within an outer casing of the apparatus, but following the destruction-free opening of the casing is accessible in such a way that it can be replaced by a freshly filled magazine body and/or its magazine chambers can be freshly filled. To this end the magazine body can be connected in non-destructive, detachable manner to a casing cover or lid, from which it can be removed when the lid is open. This lid can simultaneously form the actuating handle for indexing the magazine body and a bearing member for at least one axial and/or radial bearing.

The magazine chambers of the magazine body can also be constructed for receiving medium capsules, which are appropriately made in thin-walled manner from brittle material, so that in the case of pressure, scratching and/or puncturing action they crack, burst or break open in a larger area manner than corresponds to the engagement surface of the opening tool. Thus, during the discharge the opening tool can remain in the vicinity of the engagement with the capsule, without blocking together with the latter the feed path or the opening formed in the capsule.

In the feed path between a pressure chamber of the generator and the reception chamber or discharge opening, as well as in the transport or feed path of the medium no valves are required, so that the discharge apparatus can be constructed in valve-free manner, optionally with the exception of the inlet valve for the pneumatic pump. However, the magazine body can run with the inlet and/or outlet ends of its magazine chambers along closing surfaces, which release or open said ends in the manner of a valve control, when the particular magazine chamber is in the discharge position.

However, it is also conceivable, particularly in the flow direction upstream of the reception chamber or the magazine chamber acting as such in the discharge position, to provide a valve for the feed or delivery flow, which opens in pressure and/or path-dependent manner if a predetermined overpressure is reached in the pressure chamber or the line connection of the feed path through the reception chamber and the discharge opening has been formed or freed. As a result the relatively highly precompressed feed medium can be suddenly relaxed in the reception chamber, so that the medium contained is suddenly loosened and discharge in ultrafinely distributed form.

If a pneumatic pump is provided as the pressurized gas generator or producer, then its pressure or pump chamber is appropriately defined by the same casing part, as a casing chamber for the reception of the reception chamber or the magazine body. Therefore said sleeve or jacket-like casing part can be closed at one end closing said casing chamber and at the other end with a displaceable actuating handle, which carries a pump piston running on the inner face of said casing part. The two remote faces of said cover, which can simultaneously form the end faces of the apparatus, are suitable as pressure or actuating handles for an ergonomically favourable discharge actuation.

However, it is also conceivable that of the two subassemblies moved against one another for discharge actuation, one is substantially entirely located within the other, so that over its length the discharge apparatus is substantially bounded by a one-piece, through jacket. The outer casing of the apparatus can, with the exception of the pump-side closure, have a substantially constant external diameter or width over its entire length, or in the vicinity of the transition between the reception chamber and the generator or in the vicinity of the facing cover can have a reduction in its external width such that it can be securely gripped on two circumferential areas between the fingers for indexing or the like.

The discharge opening is advantageously formed by a discharge connecting piece projecting freely over the outer circumference and roughly in the plane of the reception magazine chamber and which is preferably placed in its longitudinal direction from the outside of the casing jacket and which is secured by a snap connection. Thus, the same discharge apparatus can be provided, as required, with different discharge connecting pieces, e.g. a discharge mandrel to be inserted in the nose or a cross-sectionally flat mouthpiece to be inserted in the mouth.

BRIEF FIGURE DESCRIPTION

These and further features can be gathered from the claims, description and drawings and the individual features, either alone or in the form of subcombinations, can be realized in an embodiment of the invention and in other fields and can represent advantageous, independently protectable constructions for which protection is hereby claimed. Embodiments of the invention are described in greater detail hereinafter relative to the drawings, wherein show:

FIG. 1 An inventive discharge apparatus in axial section.

FIG. 2 The discharge apparatus according to FIG. 1 on a reduced scale, turned view from the outside.

FIG. 3 A cross-section through FIG. 1.

FIG. 4 A cross-section through FIG. 1.

FIG. 5 A detail as a cross-section through FIG. 4.

FIG. 6 A detail of FIG. 1 on a much larger scale.

FIG. 7 A detail of FIG. 1 in cross-section and on a larger scale.

FIG. 8 A detail of FIG. 1 in a developed view.

FIG. 9 Another embodiment, partly in axial section.

FIG. 10 Another embodiment in axial section.

FIG. 11 A detail of FIG. 10 on a larger scale.

FIG. 12 A detail of the magazine body of FIG. 10 in an axial view.

FIG. 13 Another embodiment in axial section.

FIG. 14 Another embodiment in a view corresponding to FIG. 10.

FIG. 15 Another embodiment in axial section.

FIG. 16 An embodiment similar to FIG. 1.

FIG. 17 A cross-section through FIG. 16.

FIG. 18 The discharge apparatus of FIG. 16 on a reduced-scale outside view.

FIG. 19 A plan view of FIG. 18.

FIG. 20 Another embodiment in axial section.

FIG. 21 A cross-section through FIG. 20.

FIG. 22 Another embodiment in axial section.

FIG. 23 A detail of FIG. 22 in axial view.

FIG. 24 A detail of FIG. 22 in axial view.

FIG. 25 The discharge apparatus of FIG. 22 in an outside view, inverted position and turned by 90.

FIG. 26 The discharge apparatus according to FIG. 22 in the loading state.

FIG. 27 A detail of another discharge apparatus in axial section.

FIG. 28 A detail of FIG. 27 on a larger scale and in cross-section.

FIG. 29 Another embodiment in a representation form corresponding to FIG. 27.

FIG. 30 A magazine body according to FIG. 29 prior to insertion in the discharge apparatus.

DETAILED DESCRIPTION OF PREFERRED EXAMPLE EMBODIMENTS

Figure 13:
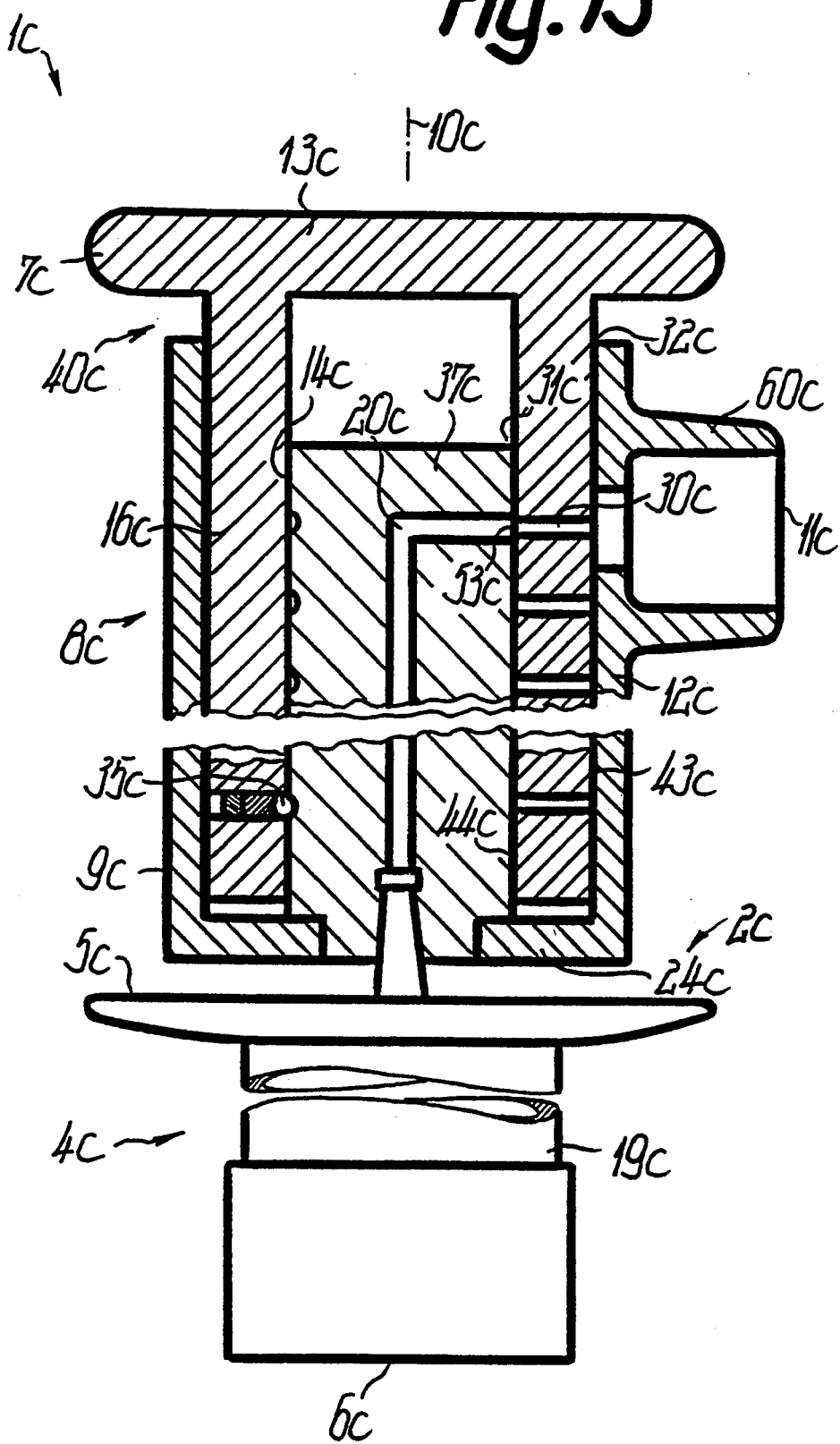

The discharge apparatus 1 has in a substantially equiaxial arrangement a discharge conveyor 2 and a manually operable discharge actuator 3, as well as a pressurized gas generator or producer 4, which can be a component of the conveyor 2 in such a way that substantially simultaneously with the actuation of the generator and through said actuation medium is conveyed or delivered. For actuation purposes two remote front or end faces of the discharge apparatus 1 are provided as handles 5, 6, which in the case of reciprocal approximation by finger pressure between the fingers of a hand bring about the discharge of a medium dosing quantity and optionally other control processes and on release automatically return to their starting position. For performing one of said control processes additionally a circumferential surface is constructed as a handle 7 and is rigidly connected to the handle 5.

The discharge apparatus 1 which is substantially formed from dimensionally stable plastic components has a dimensionally rigid, hollow basic body 8, which forms a larger longitudinal section of the outer jacket of a casing 9, whose external shape is substantially symmetrical to a central axis 10. The casing 9 has an approximately sleeve-like casing part 12 over most of its length and extending up to its outer circumference and which over its entire length has a substantially constant internal and/or external width and essentially forms the basic body 8.

At one sleeve end the casing part 12 is closed or sealed by a cap-like cover or lid 13 with roughly the same jacket width and secured against axial movements in the operating state and whose outside of its cap end wall forms the handle 5 connected rigidly to the basic body 8 in the actuation direction. The cover 13 closes in substantially dust-tight manner a casing chamber 14 bounded by the inner circumference of the casing part 12 and in which is interchangeably arranged a magazine 15 with individual portions or doses of the medium to be discharged.

The magazine 15 has an annular magazine body 16, arranged around the central axis 10 and which is ring disk-like between its inner and outer circumference. The magazine body 16 comprises two substantially identical components 17, 18 interconnected e.g. by surface welding in the separating plane, which close axially on one another and whose dividing plane is located in the common median plane of the magazine chambers 30 for the medium.

The generator 4 is substantially formed by a thrust piston or pneumatic pump 19 located in the central axis 10 and whose pump or pressure chamber 21 is to be connected on the outlet side via a feedpath 20 with a discharge opening 11 leading into the open and accompanied by the interposing of at least one magazine chamber 20. Roughly equidistantly between its ends the casing part 12 is provided with an approximately ring disk-shaped partition 22, which forms part of the pressure-tight separation between the casing chamber 14 and the pressure chamber 21. Following onto the partition 22 the inner face of the jacket of the casing part 12 forms the piston path 23 for a pump piston 25 of a piston unit of the pneumatic pump 19, so that said piston part 23 is constructed in one piece with at least one bearing surface for the magazine body 16.

The associated end of the casing part 12 is also closed by a cap,like cover 24, but which is axially displaceable with respect to the basic body 8 and which engages in the interior of the pressure chamber and forms the handle 6 with the outside of its cap end wall. The cover 24 is secured with respect to the casing part 12 to prevent removal by means of an axial, self-engaging snap connection 26 and in the vicinity of its opening cap edge having the associated snap member carries the separate, cup or ring-shaped piston 25, which is also fixed in axially self-engaging manner to the cover 24 by means of a snap connection 28.

On the piston head of the piston 25 running with a ring lip on the piston track or path 23 is supported a return or restoring spring 27 by one end and its other end is supported under pretension and centred on the partition 22 and the piston unit is loaded to the stop-limited starting position by the snap connection 26. The piston head is traversed within the snap connection 28 by an inlet channel issuing into the pressure chamber 21 and in which is appropriately provided roughly in the vicinity of the cap end wall a return or intake valve 29, so that through an opening in the cap end wall or the handle 6 air can be sucked from the outside into the pressure chamber 21 during the return stroke.

The magazine chambers 30 are substantially arranged with the same angular spacings in a ring around the central axis 10, are continuously linearly constructed, oriented radially to the central axis 10 and tightly closed against one another, the length of each magazine chamber 30 being three, four or even more than six times greater than its internal width, which is appropriately constant in smooth-walled manner over its entire length. Each magazine chamber 30 is formed from two channel or shell boundaries, so that it is easily possible to produce the components 17, 18 as injection mouldings.

The magazine body 16 is so mounted with a radial bearing 31 located on its inner ring circumference and a radial bearing 32 located on its outer ring circumference, that through said radial bearings substantially all the magazine chambers 30 can be simultaneously tightly closed. In addition, for the axial fixing of the magazine body 16 there are two axial bearings 33, 34, whereof the axial bearing 33 is formed by the ring-like, offset rotary engagement of the open cap edge of the cover 13 in the associated end of the casing part 12, whilst the oppositely acting axial bearing 34 engages on a face of the magazine body 16 facing the generator 4 or the partition 22. The axial bearing 33 simultaneously forms a radial bearing or a centring for the cover 13 with respect to the casing part 12.

The magazine body 16 can be rotated in stepwise manner about the angular division of the arrangement of the magazine chambers 30 with a catch 35, which can be formed by the axial bearing 34, is completely located within the casing chamber 14 and only allows a rotary movement in a single rotation direction in the manner of a freewheel, which is interlockingly blocked against the opposite rotation direction. At least with respect to the indexing rotation direction the magazine body 16 is substantially rigidly connected by means of a coupling 36 located within the casing chamber 14 to the cover 13 or the handle 7. This coupling 13 can be easily separated in nondestructive manner and is e.g. formed by a bayonet joint between the face of the magazine body 16 facing the handle 5 and a cross-sectionally polygonal inner sleeve of the cover 13, which projects freely from the inside of the cap end wall.

On a socket projecting into the casing chamber 14 from the partition 22 ill the vicinity of the inner circumference is mounted an inner body 37 with a sleeve end rigidly connected to the basic body 8 and surrounding the central axis 10 and which traverses the magazine body 16 and forms in the vicinity of its other sleeve end a snap member of a snap connection 38, with which the cover 13 is so secured against removal from the casing part 12 or the axial bearing 33, that it can only be axially completely removed on exceeding a predetermined removal force.

The snap members of the snap connection 38 engage radially resiliently and in rotary manner in one another and therefore form a snap mounting for the cover 13 and the magazine body 16. After removing the cover 13 the magazine body 16 is free in spaced manner from the open cover edge, so that it can be released from the cover 13 by a rotary movement and can be replaced by another magazine body 16. The cover 13 is again refitted to the basic body 8 and firstly the magazine body 16 engages with its radial bearings 31, 32 and then the cover 13 engages in the bearing 33, so that an axial plug mounting is obtained for replacement.

Within its outer sleeve associated with the radial bearing 31, the inner body 37 forms an elongated, cup-shaped, hollow core body 39 closed at the bottom and which projects through the socket or the central opening of the partition 22 into the pressure chamber 21 and with the central opening or the socket bounds an annular outlet opening for the pressure chamber 21, which is constricted in the flow cross-section compared with a following portion of the feed part 20. By means of the core body 39 which is in one piece or tight and arranged roughly in the plane of the magazine chambers 30 on the inner circumference of the outer sleeve, the pressure chamber 21 is closed in pressure-tight manner with respect to the casing chamber 14.

The control or indexing mechanism 40 for indexing the magazine body 16 is in this case a substantially stepping control mechanism operated independently from other actuations of the discharge apparatus using the handle 7 and whose control or indexing steps are determined by the catch 35. For this purpose the magazine body 6 is provided on its end face with sawtooth-like locking members 41 arranged in a ring and along which runs at least one resilient locking member 42 of the basic body 8, which can be formed by spring tongues projecting from the partition 22. In the locking position a magazine chamber 30 as a reception chamber is so oriented with respect to the feed path 20, that it is connected as a channel portion to the said path 20 and the entire medium flow flowing through the feed path 20 can only be passed on through the reception chamber 30. The magazine chamber 30 traverses a substantially cylindrical outer circumference 43 and a substantially cylindrical inner circumference 44 of the magazine body 16 and the particular circumference can be formed by a sleeve-like bearing flange, which projects axially over one or both end faces of the ring disk-like section.

On the inner circumference 44 the magazine chamber 30 with its radially inner end forms an inlet 46 and on the outer circumference 43 with its radially outer end forms an outlet 47, in each case for substantially tight connection to a following section of the feed path 20. In order that no loosening medium from the magazine chamber 30 can pass between the bearing faces of the particular bearing, the inlet 46 and/or the outlet 47 can be closed in each case by a closure member 45, which does not or only insignificantly projects over the associated passage base of the magazine body 16 and can e.g. be formed by a thin, self-adhesive or welding-fixed film or foil, which appropriately easily tears and/or is relatively brittle. The closure member 45 for all the inlets 46 or outlets 47 together can be in the form of a revenue stamp, which passes uninterruptedly over the associated circumference of the magazine body 16.

For opening the particular outlet 47 or inlet 46, in each case an opening device 50 or 51 can be provided, whose working movement is appropriately directly the rotary indexing movement of the magazine body 36, so that the opening tool 48 mounted on the basic body 8 can be substantially fixed. This appropriately steel opening tool 48, or which can be made from some other very hard material, can in the case of the opening device 51 be formed by a rod body, which is inserted in a longitudinal groove in the outer jacket of the inner body 37 traversing the snap connection 38. The opening tool can also, e.g. as in the case of the opening device 50, be a radial body with three arms projecting roughly radially to the central axis of the magazine chamber 30 oriented towards it and which is applied to the associated circumference of the magazine body 16.

In each case the opening tool 48 appropriately has a scratching cutting edge 52, which engages in much the same way as a shearing tool in a mating tool or a further opening tool 49, which can be directly formed by the magazine body 16. For example, the cutting edge 52 can engage in a circumferential groove of the magazine body bridged by the closure member 45, so that during the indexing movement the latter is necessarily slit and consequently the inlet 46 or the outlet 47 is opened.

In the jacket of the outer sleeve of the inner body 37 is provided a radial passage or connecting opening 53 connected to the annular portion of the feed path 20 and which is oriented substantially equiaxially to the magazine chamber 30 in the starting position and then at least partly coincides in the manner of a slide valve with the inlet 46. On a larger part of its circumference the connecting opening 53 is bounded by the associated opening tool, its passage width being smaller than that of the inlet 46 or the magazine chamber 30. In the vicinity of the outlet 47 the associated connecting opening 84 is bounded between the radial arms of the opening tool, which have the scratching cutting edge 45 in the node or centre of the radial body. The radial arms can be cross-sectionally bevelled, e.g. with a profile edge pointing counter to the flow direction, which lead to baffle, guidance and loosening surfaces, through which the medium flowing along the same is whirled up and optionally deagglomerated.

The connecting opening 54 is formed by the inner end of a linear end channel 55 approximately equiaxial to the reception chamber 30 and which is connected to the outlet 47 for or the connecting opening 54 with a larger flow cross-section than the latter and then passes into a conically, continuously tapering channel portion 56, whose narrowest area forms the discharge opening 11 coaxial the reception chamber 30.

The end channel 55 is surrounded by a coupling 57 positioned transversely to the central axis 10 and which is located on the outside of the casing 9 or projects roughly radially over its outer jacket 58 and has a coupling member connected in sleeve-like manner to the basic body 8. On said coupling member can be mounted from the outside an elongated discharge connecting piece 60 forming the end channel 55 or the discharge opening 11 and which is secured with a plug or snap connection 59, which is appropriately formed by the coupling 57. Apart from a jacket externally engaging over the coupling member with the snap connection 59, the discharge connecting piece 60 has an inner jacket engaging in the coupling member and whose end applies the opening tool of the opening device 50 against the circumference of the magazine body 16.

For the operation of the discharge apparatus in the described manner a magazine body 16 with filled magazine chambers 30 is inserted and then the desired magazine chamber 30, optionally with the aid of an indication detectable from the outside, is oriented by manually turning the handle 7 with respect to the casing part 12 onto the line connection to the feed path 20 or the connecting openings 53, 54. The discharge opening 11 is then brought into the vicinity of the use area and the piston 25 is manually displaced against the partition 22. Thus, compressed air flows out of the pressure chamber 21 to the connection opening 53 and presses against the inlet 46.

As soon as a given overpressure is reached, the plug-like filling of the magazine chamber 30 is expelled in the discharge direction, is loosened on the scratching cutting edge 52 and the radial arms and is then ejected through the discharge opening 11 by the following gas flow and accompanied by whirling up in the end channel 55. Following the release of the handles 5, 6, under the tension of the return spring 27, the discharge apparatus 1 returns to its starting position and the next magazine chamber 30 can be moved into the discharge position for forming a reception chamber by rotation and is then also emptied. The discharge apparatus 1 operates equally well in all positions, including the inverted position. The total length of the elongated apparatus can be below 10 cm.

In FIGS. 9 to 26 corresponding parts are given the same reference numerals as in FIG. 1, but are followed by different letter references and all description parts apply correspondingly to all the embodiments.

According to FIG. 9 the casing or cap-like basic body 8a receives substantially all the components of the discharge apparatus 1a in its interior, which gives a very smooth, continuous outer surface. From the cap opening of the basic body 8a, an opposed, also approximately cap-like cover or component 24a is inserted and by means of a widened outer collar 64 located in the vicinity of its end is prevented from rotating by groove and tongue guidance with respect to the basic body 8a, but is axially displaceable for performing the discharge actuation, A jacket shoulder projects over the inner face of the outer collar 64 and forms the piston path 23a, so that here the pressure chamber 21a is formed by the cover 24a and is displaceable with respect to the basic body 8a.

Between the outer circumference of the casing shoulder and the inner circumference of the basic body 8a the magazine body 16a is inserted with a control sleeve 65 projecting axially over its ring disk-like magazine area and with which the magazine body 16a is mounted in rotary manner on the outer circumference of the jacket shoulder. The associated axial bearing 33a is formed by a torus engaging in a circular groove, so that it simultaneously forms a radial bearing, as well as an axially separable, resilient snap connection so as to constitute the coupling 36a for releasing the magazine body 16a from the cover 24a. Adjacent to the bearing 33a, in the vicinity of the free end of the jacket shoulder, the freewheel catch 35a is provided between the outer circumference of the jacket shoulder and the inner circumference of the control sleeve 65, through which the control or indexing steps of the control mechanism 40a are at least partly defined.

An indexing drive of the mechanism 40a is provided between the outer circumference of the control sleeve 65 and the inner circumference of the basic body 8a and is formed by inclined surfaces distributed over the circumference on both components, through which in the case of reciprocal axial travel the magazine body 16a is advanced by one indexing step in opposition to the force of the catch 35a. The rotation prevention between the basic body 8a and the cover 24a occurs on the inner circumference of the basic body 8a and said means can extend into the vicinity of an outer collar of the control sleeve which has the associated inclined faces.

The piston 25a is in this case located on a piston rod 37a projecting freely from the inside of the cap end wall of the basic body 8a and which traverses the magazine body 16a in rotary and also axially displaceable manner, because the magazine body 16a is fixed with respect to the cover 24a by the bearing 33a. The piston 25a and the piston rod 37a are traversed by the feed path 20a, which passes into the connecting opening 53a located on the outer circumference of the piston rod 37a. A valve 62 constituting an outlet valve for the pressure chamber 21a is provided in the feed path 20a and has a valve body 62 spring-loaded towards the closing position in the piston rod 37a or in the piston unit.

With the valve body is associated a valve opener 63, which is mechanically opened shortly before or at the end of the working stroke of the valve 52 in that the valve body strikes on an opener mandrel projecting from the opposite end wall of the pressure chamber 21a. This valve opener 63a can form a single component with the intake valve 29a, which in turn, together with a valve casing, can be inserted in a mounting support of the end wall.

In the starting position according to FIG. 9 the next magazine chamber 30a to be emptied or its inlet 46a and/or outlet 47a are positioned in axially displaced manner with respect to the associated connected opening 53a or 54a and namely roughly by the working stroke of the pneumatic pump 19a and are advanced by one indexing step in the rotation direction. If the component 24a is now pressed into the basic body 8a in opposition to the tension of the not shown return spring, then it takes the magazine body 16a axially with it. Simultaneously the sloping faces of the indexing mechanism 40a come into engagement with one another, so that the magazine chamber 30a to be emptied during this operating cycle is rotated by a further indexing step accompanied by the overcoming of the catch 35a before the inlet 46a has reached the connecting opening 53a.

As the axial movement proceeds, the inner circumference 44a runs over the connecting opening 53a, so that the latter in the manner of a valve control is substantially tightly closed and is only released when it coincides with the inlet 46a. In this instant or shortly before it the valve 62 is opened counter to the tension of its valve spring, so that the highly compressed gas escapes suddenly from the pressure chamber 21a, through the feed path 20a and into the corresponding magazine chamber 30a. In a similar manner, by valve control the connecting opening 54a can initially be closed by the outer circumference 43a of the magazine body 16a and is then made to coincide with the outlet 47a. Here the connecting opening 54a and the discharge opening 11a are formed by the inner or outer end of a through,opening in the jacket of the basic body 8a. In order that the handle 6a is readily accessible over the entire working stroke, at least one finger cutout 66 is provided in the jacket of the basic body 8a and this cutout emanates from the open end face of the basic body 8a and its height roughly corresponds to the working stroke.

The discharge apparatus 1b according to FIGS. 10 to 12 has magazine chambers 30b roughly axially parallel to the central axis 10b and which traverse the two faces of the magazine body 16b or are closed by the bearing faces of the axial bearings 33b, 34b located on said faces. The connecting openings 53b, 54b are located in the corresponding faces of the e.g. disk-shaped basic body 8b and the also substantially disk-shaped, facing body 13b, which in this case is constructed in one piece with the discharge connecting piece 60b.

Between the two bodies 8b, 13b, which are braced against one another by a bolt 31b forming a radial bearing and are prevented from rotating, there is a magazine body 16b mounted in rotary manner on the bolt 31b and whose outer circumference is at least accessible over part of its extension so as to serve as a handle 7b for turning. The generator 4b or the pneumatic pump 19b is in this case connected optionally in easy, non-destructive, detachable manner to the discharge apparatus 1b by a line plug coupling, so that after emptying it can be replaced by a new discharge apparatus, which is then to be connected once again by a plug connection to the pneumatic pump 19b, a propellant gas container or the like.

The generator 46 is eccentric to the rotation or central axis 10b roughly by the radius of the ring of magazine chambers 30b. The catch 35b between faces of the magazine body 16b and the basic body 8b running on one another accordingly eccentric, the basic body 16b having in a ring radially outside the magazine chambers 30b locking depressions, in which engages a spring-loaded locking ball.

The inlet 46b or the filling chamber of the particular magazine chamber 30b is set back against the associated face, so that a roughly equiaxial thereto, but widened casing chamber is formed for receiving a screen or sieve 67 and/or a seal 68. The screen 67 is located in the form of a flat screen disk on a ring shoulder of the casing chamber surrounding the inlet 46b and which is formed by a corresponding depression in the associated passage or end face of the magazine body 16b.

The rubber-elastic seal 68 constructed as an O-ring presses the screen 67 against the ring shoulder and runs with its side remote therefrom on the associated face of the basic body 8b with axial pressure, so that on orientation with respect to the connecting opening 53b, it forms a seal for the feed path 20b. A corresponding seal or screen could also be provided in the vicinity of the outlet 47b or the connecting opening 54b. The screen 67 forms a closure for the associated end of the magazine chamber 30b, which although permeable for the feed gas, it is not readily permeable for the medium. The basic body 8b and the component 13b can also be constructed in one piece or engage over part of the outer circumference and/or cover in casing-like manner the magazine body 16b.

According to FIG. 13 for indexing the magazine body 16c is linear and guided roughly parallel to the central axis 10c, the magazine chambers 30c being provided in parallel succession in said longitudinal direction. The magazine body 16c has a sleeve-like construction and extends roughly over the entire length of the basic body 8c, the casing 9c or the cross-sectionally annular casing chamber 14c, which is bounded on the outer circumference by the sleeve or cup-shaped casing part 12c and on the inner circumference by the rather shorter inner body 37c, which can also project in one piece from the end or base wall 24c of the casing part 12c and is traversed by the feed path 20c. The magazine body 16c is inserted from the open cup side into the casing part 12c and has at its end located outside said part 12c a disk collar 13c projecting over its outer circumference and which forms the handle 7c fox the axial displacement with respect to the basic body 8c.

On the side remote from the connecting opening 53c is provided the catch 35c for the magazine body 16c, which e.g. has a locking member roughly radially resiliently loaded in the jacket of the magazine body 16c and for each magazine chamber 30c a locking opening on the outer circumference of the inner body 37c. If the magazine body 16c is not prevented from rotating with respect to the basic body 8c, but is instead mounted in rotary manner, then in each plane, at right angles to the central axis 10c and similar to FIG. 1 it is possible to provide several magazine chambers 30c or catches 35c, so that both by rotating and also by axial displacement indexing can occur and optionally in individual planes can be kept ready individual media or doses for discharge purposes. The discharge connecting piece 60c is constructed in one piece with the basic body 8c or the inner body 37c, which are to be interchangeably connected to the generator 4c.

The discharge apparatus 1d according to FIG. 14 has a similar construction to that of FIGS. 10 to 12, but the magazine chambers 30d can be automatically filled from a storage magazine 69 using a refilling device 70 and which has a much larger storage capacity than the reception capacity of the magazine chamber or chambers 30d. At least one shaft-like, storage magazine 69 having approximately internal cross-sections over its entire length, projects over the end of the basic body 8d remote from the magazine body 16d, so that it can project freely e.g. in roughly the same direction as the discharge connecting piece 60d or the generator 4d and can be connected from the associated end to the magazine body 16d.

The storage chamber of the storage magazine 69 having roughly the same width as the magazine chamber 30d is connected by means of a short passage opening 71 to the magazine chamber 30d coinciding therewith, said opening 71 being cross-sectionally slightly constrictable compared with the storage chamber and/or the magazine chamber 30d, so that on passing over the medium is slightly compressed and can then loosen or expand again in the magazine chamber 30d. At the end remote from the passage opening 71 the storage chamber is bounded by a displaceably guided piston 72, which with the decrease in the storage quantity follows along by the force of weight, spring tension and/or vibrating movements, so that the stored medium is always loaded towards the passage opening 71 and is kept in uniformly compressed structure in the storage chamber.

The passage opening 71 coaxial to the storage chamber can be displaced e.g. by roughly 180° or an arc angle diverging therefrom about the rotation axis 10d with respect to the connecting openings 53d, 54d and can be arranged in such a way that on orienting a magazine chamber 30d with respect to the connecting openings 53d, 54d a different magazine chamber 30d is connected to one or more passage openings 71. The magazine body 16d can have one, two or more magazine chambers 30d. The casing parts 12d, 13d engaging over or mounting the magazine body 16d at both end faces can be constructed in one piece with one another or formed by the basic body 18d, which can also be a casing 9d surrounding the magazine body 16d over most of its circumference. Prior to the first use all the magazine chambers 30d and the storage magazine 69 can be completely filled, so that a relatively large storage capacity is obtained. The storage magazine 69 can be mounted in interchangeable manner on the basic body 8d and/or can have a refillable construction and for this purpose, e.g. on an end remote from the passage opening 71 can be provided with an easily removable cover.

According to FIG. 15 the reception chamber 30e is formed by a section of the feed path 20e directly following the valve 62e or the associated valve spring and which passes from the chamber 30e to the discharge opening 11e in linear manner and has a constant width over most of its length. In the wall of the tubular inner body 37e is provided a linear, approximately radial passage opening 71e, which traverses the inner circumference of both the reception chamber 30e and the roughly equally wide storage magazine 69e, which is separated from the chamber 30e by only one partition. For transferring a medium dose from the storage magazine 69e through the passage opening 71e into the reception chamber 30e there is a rod or bolt-like slide 16e, whose free feed end in the starting position is close to the bottom within the medium in the storage magazine 69e. This end of the slide 16e can be provided with a rounded scoop, a spoon 73 or a taper having a support surface pointing roughly in the outflow direction from the reception chamber 30e, so that it inserts the medium taken from the storage magazine 69e in which-like manner into the passage opening 71e and can bear in the manner of a chamber bottom in the end position within the reception chamber 30e. The spoon 73 is so small, that over most of the circumference of the reception chamber 30e it is spaced from its inner circumference and a flow can take place around it.

The slide 16e is mounted displaceably counter to the tension of a return spring roughly radially to the central axis 10e in a guide 31e of the basic body 8e and one end or the actuating section 74 projects over the outer jacket 58e of the basic body 8e. The end face of this actuating section 74 engages on a control cam 65e, which is formed by the inner circumference of the jacket of the handle 6e, which also forms the piston path 23e. Depending on whether the control cam 65e is constructed as a circumferential and/or as an axial curve, rotary and/or axial movements of this component of the handle 6e with respect to the basic body 8e lead to linear movements of the slide 16e at right angles thereto.

During the actuating stroke of the generator 4e initially the spoon 73 is transferred by the passage opening 71e adapted closely to its cross-section with medium into the centre of the reception chamber 30e and simultaneously the air is precompressed in the pressure chamber 21e and then the spoon 73 remains in the said discharge position and then the valve 62e is opened by the valve opener 63e, so that air flows at a high speed round the spoon 73 from the rear and entrains the medium. In the discharge position the spoon 73 consequently forms as a displacement body a constriction of the flow cross-section of the feed path 20e, but only in the vicinity of the reception chamber 30e.

The pump piston 25e is fixed by means of the snap connection 28e to the rear end of the basic body 8e in the flow direction of the feed path 20e and immediately adjacent to the partition 22e, which is only removed from said end by roughly the length of the snap connection 28e. The pump piston 25e can have roughly the same external diameter as the basic body 8e, which on the outer jacket 58e is overengaged by the piston path 23e and the control cam 65e of the indexing mechanism 40e for the slide 16e. The generator 4e or the pressure chamber 21e is consequently immediately adjacent to said end of the basic body 8e or the casing chamber 14e. The medium in the storage magazine 69e is admittedly loaded by a piston 72e towards the spoon 73, but it is appropriate to provide a vibrator 75 for the cavity-free provision of the medium in the vicinity of the spoon 73 and as a result of a ratchet tooth system or the like automatically produces vibrations during the lifting movement and/or by separate actuation, which act on the storage magazine 69e or the associated component. Instead of providing a ratchet tooth system between the stroke components 6e, 8e movable against one another it is also possible to provide directly on one of these components, e.g. on the basic body 8e, a vibrating ratchet with teeth of a tooth system 77 jumping over one another during operation. On a toothed portion of the outer circumference 58e of the basic body 8e directly connected to the cover 13e is mounted in rotary manner a ring 76e having an inner tooth system, which can be manually turned by engaging on the outer circumference, so that the said vibrations are produced, which compress the medium in the storage magazine 69e around the spoon 73 in an adequate manner. The storage magazine 69e is axially parallel to the adjacent portion of the feed path 20e within the casing chamber 14e in the transverse direction.

The discharge apparatus 1f according to FIG. 16 has a similar structure to that of FIGS. 1 to 8, but instead of being directly received in the magazine chambers 30f, the medium is received in prepacked, tightly closed elongated capsules 80, which over their entire length have an approximately constant, cylindrical external width or diameter, as well as spherically rounded ends and appropriately are made from a moisture-stable, brittle plastic. The opening tool of the opening device 50f or 51f has an injection or spraying mandrel 52f projecting into the arcuate indexing path of said end and which is appropriately polygonal, e.g. triangular or quadrangular in cross-section. On engaging the capsule end in the discharge position it runs onto the mandrel 52f, so that it can be opened by shattering or non-shattering damage and only under bending deformation, as well as by cracking and consequently forms the inlet 48f or the outlet 47f. Following discharge, the empty capsules are left in the magazine body 16f, which is replaceable in the described manner by a filled body.

The connecting opening 54f issues in this case into a significantly constricted nozzle 78, which is equiaxial to the connecting opening 54f, is connected to the acute-angled, conical constriction 56f and has an axial spacing from the connecting opening 54f, which is roughly of the same order of magnitude as its width. However, the axial spacing with respect to the discharge opening 11f is much greater. The nozzle 78 issues roughly centrally and equiaxially into the end channel 55f which is only slightly or not constricted compared with the discharge opening 11f and which is much wider than the nozzle and the connecting opening 54f and in which it delivers the initially compressed mixture flow in the manner of an atomizer nozzle. The end channel 55f or the discharge opening 11f and the discharge connecting piece 80f can have flat cross-sections, which leads to a mouthpiece readily insertible between the lips.

The generator 4f has an external diameter reduced compared with the basic body 8f and the casing chamber 14f, which extends up to the associated side of the partition 22f, so that the casing part 12f forms two width, reciprocally offset portions of roughly the same length. In the centre of the end wall of the cover 13f a cup-shaped projection 79 projects axially, so that the handle 5f is then constructed in annular manner on the outer circumference of the casing 9f and as a result the discharge apparatus 1f can be particularly well gripped with one hand, guided in oriented manner and operated.

In the case of the discharge apparatus 1h according to FIGS. 20 and 21 the handle 5h is closer to the end of the basic body 8h or the casing 9h associated with the handle 6h than to the other end and it can be connected to the rear end of the basic body 8h. The handle 5h projects in the manner of a cross-web or a ring disk at least at two remote sides over the outer circumference 59h of the casing 9h so that it is possible to support thereon an index and middle finger, accompanied by the interposing of the casing 9h. The thumb is supported on the handle 6h. The basic body 8h is constructed in elongated roughly rod-like manner in the central axis 10h and adjacent to the end associated with the discharge opening 11h has in its jacket a window 81, in the vicinity of which the circular disk-like magazine body 16h is mounted eccentrically and rotatably roughly parallel to the central axis 10h.

The rotation axis formed by the pivot pin 31h is positioned between the inner and outer circumference of the casing jacket, so that at least one magazine chamber 30h not in the discharge position can be located wholly or partly on the outside of the casing 9h or within the window 81 and the magazine body 16h is accessible for indexing immediately on said outside. The magazine chamber 30h or magazine body 16h is shorter than the capsule 80h, so that the latter with one or both ends projects over the magazine body 16h by roughly the same distance at least by its spherical end and is positionly secured by circumferential jamming with respect to the magazine chamber 30h. In the discharge position the inlet-side end of the capsule 80h is in a shell-like depression surrounding the connecting opening 53h, which positionly secures the capsule 80h or the magazine body 16h in the manner of a catch which can be resiliently overcome and here for the catch means use is made of the resilient deformation characteristics of the capsule 80h. The outlet-side end of the capsule 80h can be provided in the discharge position within the end channel 55h with a spacing from the discharge opening 11h, which is approximately the same or smaller than the length of the capsule 80h. The connecting opening 53h is much narrower than the portion of the end channel 55h surrounding in annular manner with radial spacing the capsule 80h. In opposition to the drawing representation, the window 81 can be so narrow that it is substantially closed or sealed with respect to the channel 55h by the magazine body 16h or at least a capsule 80h in each discharge position.

For opening the inlet and outlet of the capsule 80h is provided an opening device 50h, which is attached as a closed subassembly on the basic body 8h for opening purposes and after opening can be completely removed or swung to the side, if it is movable with its basic body between an opening position and an inoperative position, e.g. it is pivotably mounted on the basic body 8h. The basic body is constructed as an approximately sleeve-like plug body 82, which with a reduced plug projection can be inserted in the discharge opening 11h or the channel 55h in centred manner roughly parallel to the central axis 10h. In the plug body 82 is displaceably mounted counter to the tension of a return spring with a handle 83 a perforating needle 52h to constitute the opening tool and is then roughly equiaxial to the capsule 80h in the discharge position.

The perforating needle 52h can be moved so far through the entire capsule 80h, that it firstly opens the outlet-side end and then the inlet-side end by perforation. This leads to a longitudinal channel circumferentially bounded by the compressed medium and which links the inlet to the outlet. The perforating needle 52h appropriately has an acute-angled, conical end tip and is only axially movable to the extent that it penetrates the inlet-side end of the capsule 80h only with part of the tip length. Therefore the inlet is opened over a smaller width than the outlet due to a corresponding stop limitation of the perforating needle 52h.

The basic body 8h passes in one piece from the end or discharge opening 11h to the remote end of the pressure chamber 21h, which is closed at the associated end of the basic body 8h for stop securing of the pump piston 25h in the discharge position by means of an annular cover 24h. The latter is traversed by the piston rod 37h, which can be constructed in one piece with the pump piston 25h and/or the handle 6h. The portion of the feed path 20h located between the pressure chamber 21h and the connecting opening 58h is linear and of constant width, including the connecting opening 53h. The connecting opening 53h or the depression surrounding it can be formed by the end of a freely projecting sleeve attachment, which is annularly surrounded in radially spaced manner by an inner circumference wider than the capsule 80h and whose front end in the discharge direction is substantially tightly closed by the associated face of the magazine body 16h, so that here an annular pressure chamber connected to the connecting opening 53h is formed and from which any inflowing air can only escape through the interior of the capsule 80h.

This air flows through the longitudinal medium channel produced by the perforating needle 52h which removes it, accompanied by whirling up, from the wall of said longitudinal channel and entrains the same, so that it is discharged in fine, uniformly whirled up manner at the outlet of the capsule 80h. The opening 11h can also serve for interchangeably arranging the discharge connecting piece with respect to the opening device 50h for the use of the discharge apparatus 1h.

The discharge apparatus 1k according to FIGS. 22 to 26 serves to receive only a single dose or capsule 80k for the medium and is refilled from the exterior after each use. It is substantially symmetrical to the central axis 10k over its entire length, but the handle 5k projects further on both sides in a transverse direction over the outer circumference of the casing 9k than in the transverse direction at right angles thereto. In the vicinity of the casing chamber 14k, the basic body 8k is engaged over in non-destructive, detachable manner at the outer circumference by a plug sleeve 38k of the cover 13k and in this case the discharge connecting piece 60k forms a component with the cover 13k and in the centre projects freely over the outside or pressure face of the handle 5k.

The single magazine or reception chamber 30k is formed by two longitudinally connected, sleeve-like chamber parts 17k, 18k, which in the discharge position are tightly engaged with their facing end faces or can also be spaced from one another, because the inserted capsule 80k can bridge any gap between the chamber part 17k, 18k as a sealing jacket. Accompanied by the interposing of the opening tool of the opening device 50k, the chamber part 17k can be placed as a separate component in a mounting opening of the cover 13k or the discharge connecting piece 60k and said opening can in simple manner be formed by the inner circumference of the feed path 20k located immediately upstream of the nozzle 78k.

The chamber part 17k projects freely with its open end into the casing chamber 14k and over the inside of an end wall of the cover 13k, which is roughly in the plane of the handle 5k and over which projects in the same direction the plug sleeve 38k. The other chamber part 18k projects in the opposite direction freely over the partition 22k with which it can be constructed in one piece, so that here the connecting opening 53k is positioned approximately in the partition 22k and directly on the associated end of the pressure chamber 21k. Therefore the inserted capsule 20k is directly adjacent to the pressure chamber 21k by its inlet-side end.

The opening tool 48k of the opening device 51k is positioned substantially within the pressure chamber 21k, being applied to its associated end face in raisable manner counter to the tension of a spring, so that the perforating mandrel 52k projects into the connecting opening 53k. For the spring loading of the opening tool 48k it is possible to provide a return spring 27k, so that the spring tension rises in path-dependent manner or with increasing actuating stroke.

For the loading or charging of the discharge apparatus 1k the cover 18k is removed from the basic body 8k and a capsule 80k is inserted in the chamber part 18k in such a way that it projects over its free end and engages with its end face on the perforating mandrel 52k. The cover 13k is then fitted in such a way that the chamber part 17k receives the projecting end of the capsule 80k, said end striking in the chamber part 17k, so that the capsule 80k is entrained in its stop position with respect to the chamber part 18k. The capsule can carry along the opening tool 48k in opposition to the tension of the spring 27k, so that it is initially not or not completely opened. With the start of the operating stroke of the pneumatic pump 19k, there is a rise in the spring tension acting on the opening tool 48k in the opening direction until the perforating mandrel 52k, under said tension, penetrates the capsule 80k, opens it and consequently forms inlet, which then in the manner of a valve to be opened by destruction releases the feed path 20k. The opening tool of the opening device 50k can be rigidly mounted, so that on engaging the cover 13k or prior to the opening of the inlet it leads to the opening of the outlet of the capsule 80k.

The end channel 55k in which the nozzle 78k issues is narrower than the outer circumference of the discharge connecting piece 60k by significantly more than its smallest or largest wall thickness and said piece has approximately flat oval or flat diamond shaped external cross-sections with a minimum width, which corresponds to the external width or diameter of the tube portion bounding the end channel 55k. This tube portion constructed in one piece with the remaining discharge connecting piece 60k is connected at two remote sides blind chambers, which are bounded by the connecting piece 60k and are open roughly in one plane with the discharge opening 11k, but are otherwise closed. Therefore the discharge connecting piece 60k despite a narrower, substantially cylindrical construction of the end channel 55k is suitable as a mouthpiece, which can be inserted in the mouth and received between the lips in external circumferentially sealed manner.

The discharge apparatus 1m according to FIGS. 27 and 28 has a magazine body 16m, in which for the reception chambers 30m radial grooves are only provided in the face of one component 17m, whereas the other component 18m has an end or sliding face sealing said grooves at their open longitudinal sides. This annular component 18m is in cross-section through the particular annular portion U-shaped, engages with its U-legs around the other component 17m on the inner and outer circumferences and is connected to form a subassembly with said component 17m by means of axially formed snap connections and which serve to form the radial bearings 31m, 32m and also the axial bearings. The component 17m is fixed or in one piece with the cap 13m. To this end the cap 13m has support projections 36m projecting from the inside of its end wall and which have on their free ends circular disk-like end part forming the component 17m. This end part has on the inner and outer circumference in each case a ring collar projecting over the support projections 36m, which forms a snap member of the associated snap connection 31m, 32m. The complete magazine body 16m, including the component 18m, thus forms a closed preassembled unit with the handles 5m, 17m, which can be removed as a whole from the basic body 8m for replacing the magazine 15m. After drawing off the component 18m, accompanied by the disengagement of the snap connections, the reception chambers 30m are open over their entire length and can therefore be refilled and closed by the snapping to of the cover 18m.

In this case the component 18m also closes the inlets 46m and outlets 47m of all those reception chambers 30m which are not in the discharge position using the inner or outer U-leg. These legs are traversed by short intermediate channels aligned with the connecting openings 53n, 54n in the area in which there is a reception chamber 30m in the discharge position. The component 17m can be slidlingly turned with respect to the component 18m with the handle 7m and which is positionally secured with respect to the basic body 8m by an axially engaging and disengaging rotation preventing means and is precisely oriented with respect to the connecting openings 53n, 54n. On turning the face of the component 17m traversed by the reception chambers 30m runs onto the inner, planar face of the component 18m in such a way that the reception chambers 30m always remain tightly closed on their groove longitudinal side. Correspondingly the inlets 46m, 47m remain tightly closed by the inner circumferential surfaces of the component 18m. The magazine chambers 30m consequently only traverse the outer and inner circumference of the component 17m and not the component 18m. For better sealing purposes the faces sliding on one another can be coated with sealing and sliding coatings. The described planar closure permits a very easy filling of the reception chambers 30m and also on replacing the magazine 15m the sealing and/or bearing surfaces are always replaced, so that wear phenomena can be kept within limits.

The jacket of the cover 13m forming the handle 7m engages over the casing part 12m of the outer circumference. The catch 35m is located between the inner circumference of the cover 13m and the outer circumference of the casing part 12m, the resilient locking members 41m being constructed in one piece with the cover 13m in the form of elongated locking tongues and engage in a tooth system on the outer circumference of the casing part 12m. On removing the cover 13m, the locking members, like the rotation preventing means of the component 18m, automatically become disengaged and are automatically engaged on inserting the cover. The inner body 37m is constructed in one piece here with the basic body 8m.

The discharge apparatus in according to FIGS. 29 and 30 has a magazine 15n, in which prior to insertion in the discharge apparatus the inlet apertures 46n and the outlet apertures 47n of all the reception chambers 30n are in each case jointly closed by two coaxial, sleeve-like closure members 45n. The outer, dimensionally stable and through constant external and/or internal cross-section-possessing closure member 45n extends over the entire length of the magazine body 16n, so that it not only forms an outer protective jacket, but also a protection for the end faces of the magazine body 16n. The inner, correspondingly constructed closure member 45n only extends over the length of the inner hub of the magazine body 16n, which has the same length as the total length of the magazine body 16n, but is longer than the outer hub.

The opening tools 50n, 51n for the outer and inner closure member 45n are in this case formed on the one hand by the associated, annular face on the end of the casing part 12n located at the cover 13n and on the other by the end faces of the snap spring of the snap connection 38n, which appropriately have in each case the same external and/or internal diameter as the associated closure member 45n. For inserting a magazine 15n the magazine body 16n provided with the closure members 45n is axially inserted in the open side of the cover 13n up to a stop position. The closure members 45n remain in their closed position. If the cover 13n connected to the magazine 15n to form a subassembly is now mounted on the basic body 8n, the faces of the closure members 45n remote from the cover end wall strike against the opening members 50n, 51n, so that on further insertion of the magazine body 16n in the casing part 12n they remain facing the same, can be axially stripped off from the magazine body 16n and moved into the cover 13n.

At the end of this movement the snap connection 38n engages, so that the operating position of all said parts is secured. The closure members 45n are then stored within the cover 13n and can contribute to an improvement of its mechanical strength. During movement the closure members 45n also free the inlets 46n and the outlets 47n, so that the latter are then closed by the associated inner sliding faces of the casing part 12n. If the magazine 15n has been emptied and is replaced, then also the closure members 45n can be easily removed from the cover 13n.

The coupling 36n for the interlocking rotary driving of the magazine body 16n by the handle 17n is formed here by two telescopically interengaging sleeves, which have a shape diverging from a circular cylindrical shape and are flattened in complementary manner at a circumferential point in the manner of a circular sector. As a result the magazine body 16n can only be assembled with the cover 13n in a single rotation position and appropriately the driving sleeve projecting from the inside of the end wall of the cover 13n is located on the inner circumference of the counter sleeve of the magazine body 16n. This counter sleeve simultaneously forms the radially outer bearing hub of the magazine body 16n. In the operating position the outer closure member 45n engages closely on the inner circumference of the jacket of the cover 13n and surrounds with radial spacing the outer circumference of the coupling sleeve. Within the latter can be provided with radial spacing a further inner sleeve of the cover 13n, on which, in the operating position, the inner closure member 45n can be so engaged with its outer circumference connected correspondingly narrowly or by frictional resistance, that its inner circumference does not hinder the locking position of the locking members of the snap connection 38n associated with the cover 13.

The discharge apparatus can also be provided with an indicator 85 according to FIG. 27 with which it is possible to detect, store and indicate random data, e.g. the number of emptied or still filled magazine chambers 30m. The indicator 85 can be formed in simple manner by a window running in front of a scale and located between two components rotatable against one another, e.g. by a window in the jacket of the cover 13m and a scale on the outer circumference of the casing part 12m, the indicating window only rendering visible a single scale unit from the outside of the discharge apparatus 1m.

The features of the embodiments have been shown and represented in their particular combination, but they can also be provided in random further combinations and/or additions to further embodiments according to the invention. In particular, the features of the basic body and casing, as well as the handles, magazines or magazine bodies, feed paths, opening devices, end channel construction, indexing drives, control means and refilling means can be combined in this way. It is also possible to combine into a subassembly two or more identical and/or different discharge apparatuses 1, 1a, 1b, 1c, 1d, 1e, 1f, 1h, 1k, 1m, 1n, e.g. in order to be able to discharge different media simultaneously and/or successively.

We claim:

1. A media dispenser comprising:
    a discharge actuating means (3) for manually operating said dispenser;
    a discharge conveyor (2) for transporting said media;
    a discharge outlet (11) for discharging said media to an outside environment;
    a media magazine (15) that is insertable into said dispenser (1) to provide at least one individual magazine chamber (30) for receiving at least one dosage unit, said media magazine (15), when inserted, being operationally displaceable in a transverse direction between a discharge position and an inoperative position of said magazine chamber (30), said magazine chamber (30) having remote first and second chamber ends (46, 47), duct means (20) for conducting a conveyor stream of a conveyor medium into said magazine chamber (30), for entraining said dosage unit in said conveyor stream, and for expelling said conveyor stream commonly with said dosage unit out of said magazine chamber (30) towards said discharge outlet (11), said magazine chamber (30) being disconnected from said duct means (20) in said inoperative position, and said dispenser (1) defining a dispenser axis (10), wherein in said discharge position said magazine chamber (30) is oriented transverse to said dispenser axis (10), said first and second chamber ends providing radially inner and outer chamber ends, and control means are provided for passing said conveyor stream through said magazine chamber (30) between said radially inner and outer chamber ends (47).

2. The dispenser according to claim 1, wherein a manually operable compressed gas generator (4) is provided for feeding said conveyor stream, said gas generator (4) being located substantially coaxial with said dispenser axis (10) and axially directly adjacent to a magazine reception (14) provided for receiving said media magazine (15).

3. The dispenser according to claim 2, wherein at least one common outer jacket casing (9) is provided, said jacket casing providing an externally free outer jacket, a reception space (14) for said at least one magazine chamber (30) and at least one pressure chamber (21) of said gas generator (4), said reception space (14) and said pressure chamber (21) having substantially equal inner radial width extensions.

4. The dispenser according to claim 3, wherein said jacket casing (9) has a sleeve-shaped outer casing body (12) having remote sleeve ends and a partition (22) spaced from said sleeve ends, an inner body (37) for mounting said magazine chamber (30), an end cover (13) for detachably closing said reception space (14) at an open end, a pump piston (25) and at least one operating handle (6) inserted from an end of said casing body (12) remote from said open end into said casing jacket (9).

5. The dispenser according to claim 3, wherein said outer jacket of said casing (9) is formed by at most three components (12, 13, 24) longitudinally joined by snap connections (26, 38), said outer jacket having a coupling projection (57) for connectingly receiving a discharge dose (60) from an external outside of said jacket casing (9).

6. The dispenser according to claim 2, wherein a magazine body (16) of said media magazine (15) has an inner circumference providing said first chamber end (46), an outlet duct of said gas generator (4) being connectable to said first chamber end by displacing said magazine chamber (30) into said discharge position.

7. The dispenser according to claim 2, wherein in an initial state of said actuating means (3a) said at least one magazine chamber (30a) is closed with respect to said duct means (20a) at at least one of said chamber ends, control means being provided for opening said at least one magazine chamber (30a) as a function of actuating said discharge actuating means (3a).

8. The dispenser according to claim 7, wherein said control means comprises a linear slide control.

9. The dispenser according to claim 7, wherein said control means comprises a rotary slide control.

10. The dispenser according to claim 7, wherein said control means comprises a path-dependent positive control of a valve (62) traversed by said duct means (20a).

11. The dispenser according to claim 2, wherein at least one of said magazine chamber (30) has a control jacket (65) engaging between an inner jacket of said gas generator (4a) and an outer jacket of an actuating handle (5a) of said actuating means (3a), a magazine body (16a) containing said at least one magazine chamber (30a) being displaceably traversed by a piston rod (37a) of said gas generator having a pump piston (25a) traversed by said duct means (20a) and at least partially directly exposed with respect to said magazine body (16a) free of intermediate boundaries, said pump piston (25a) being located within said control jacket (65) in at least one position.

12. The dispenser according to claim 1, wherein a plurality of magazine chambers (30) are provided in said media magazine (15) which has a magazine body (16), said magazine chambers (30) being stepwise displaceable into said discharge position one after the other, and each of said magazine chambers (30) providing a duct section of said duct means (20) in said discharge position, said duct section extending between said radially inner and outer chamber ends (46, 47) and being oriented transverse with respect to said dispenser axis (10).

13. The dispenser according to claim 12, wherein said magazine body (16h) is arranged eccentrically with respect to said dispenser axis (10h).

14. The dispenser according to claim 12, wherein said magazine body (16h) is rotatably mounted and circumferentially partly exposed for providing a rotation handle (7d).

15. The dispenser according to claim 12, wherein said magazine body (16h) is mounted on an eccentric pivot pin (31h).

16. The dispenser according to claim 12, wherein said magazine body (16h) has a rotating portion that is aligned with a window (81) of an outer jacket casing (9h).

17. The dispenser according to claim 12, wherein said magazine body (16h) is manually accessible from outside the dispenser.

18. The dispenser according to claim 1, wherein said duct means (20) provides at least one connecting portion (53, 54) for substantially sealingly connecting at least one of said first and second chamber ends (46, 47) to said duct means (20) when said magazine chamber (30) is displaced from said inoperative position to said discharge position.

19. The dispenser according to claim 18, wherein said magazine chamber (30) has at least one of said first and second chamber ends (46, 47) that is at least partly closed by at least one closure member (45), at least one opening device (50, 51) being provided for operationally opening said closure member (45) during displacement of said magazine chamber (30) from said inoperative position to said discharge position and during connection of said magazine chamber to said duct means (20).

20. The dispenser according to claim 19, wherein said magazine has a plurality of magazine chambers (30) and said closure member (45) is common for a plurality of said magazine chambers (30).

21. The dispenser according to claim 1, wherein said medium chamber (30) is provided for directly receiving said dosage unit without additional incapsulation.

22. The dispenser according to claim 1, wherein a magazine body (16) of said magazine (15) has an inner circumference providing said first chamber end (46) and an outer circumference providing said second chamber end (47), said magazine body (15) being displaceable in a rotary motion and an axial motion, and wherein said radially inner and outer chamber ends (46, 47) are both open in said discharge position.

23. The dispenser according to claim 1, wherein at least one of said magazine chamber (30) is oblong and has a longitudinal extension transverse to said dispenser axis (10).

24. The dispenser according to claim 1, wherein a manual drive (40) is provided for displacing said magazine chamber (30) to said discharge position, said manual drive (40) providing a handle (7) rotatable about said dispenser axis (10) and at least partly separate from said magazine (15).

25. The dispenser according to claim 24, wherein said media magazine (15) is provided by a magazine body (16) bounding said at least one magazine chamber (30), said magazine chamber (30) being displaceable transverse to said dispenser axis (10), said handle (7) being directly positively connected to said magazine body (16) and at least partly providing a component separate from said magazine body (16), a coupling (36) interconnecting said handle (7) and said magazine body (16) at an end face.

26. The dispenser according to claim 24, wherein catch means (35) are provided for resiliently and releaseably locking said magazine chamber (30) in said discharge position said magazine chamber (30) defining remote first and second magazine sides, said manual drive (40) engaging on said first magazine side and said catch means engaging on said second magazine side.

27. The dispenser according to claim 24, wherein said magazine chamber (30) is provided in a magazine unit mounted entirely replaceably in a magazine reception (14), said handle (7) providing a removeable cover (13) for closing and opening said magazine reception (14).

28. The dispenser according to claim 1, wherein in said inserted state said magazine chamber (30) is axially held by a snap connection (38) provided by first and second snap members, said snap members performing a reciprocal slide motion when said magazine chamber (30) is displaced to said discharge position.

29. The dispenser according to claim 1, wherein said magazine chamber (30) defines a longitudinal plane, said magazine chamber (30) being bounded by two magazine components (17, 18) joined substantially along said longitudinal plane.

30. The dispenser according to claim 1, wherein said magazine chamber (30) defines an overall longitudinal extension, said magazine chamber (30) being bounded by an least two magazine components (17, 18) extending substantially over said longitudinal extension, said magazine components (17, 18) being displaceable with respect to each other for opening and closing said magazine chamber (30).

31. The dispenser according to claim 1, wherein at least one magazine chamber (30) provides radially inner and outer chamber sections, said first chamber end (46) being provided on said radially inner chamber section and said second chamber end (47) being provided on said radially outer chamber section, said first chamber end (46) being provided for introducing said conveyor stream into said magazine chamber (30).

32. The dispenser according to claim 1, wherein in said discharge position said magazine chamber (30) is oriented substantially coaxial with said discharge outlet (11) and is oriented substantially radially with respect to said dispenser axis (10).

33. The dispenser according to claim 1, wherein a storage magazine (69) is provided for receiving a plurality of individual dosage units of the media for successive discharge, at least one refilling device being provided for refilling said magazine chamber (30d) from said storage magazine (69) by pressing the dosage unit of the media into said magazine chamber (30d).

34. The dispenser according to claim 33, wherein at least one medium slide (16e) is provided for transferring the medium from said storage magazine (69e) at least one magazine chamber 30e, said medium slide being movable via a passage opening 71e of a partition between said storage magazine (69e) and said magazine chamber 30e.

35. The dispenser according to claim 34, wherein two casing parts of an externally outer jacket casing (9e) are provided for actuating said medium slide (16e) as a function of an actuating path, said casing parts being manually displaceable against one another, a control cam (65e) for controlling at least one of said medium slide (16e) passing in one piece into a piston path (23e) provided for generating the secondary feed flow.

36. The dispenser according to claim 34, wherein said medium slide (16e) has a substantially linear displaceability.

37. The dispenser according to claim 34, wherein said medium slide (16e) has a displaceability transverse to said feed path (20e).

38. The dispenser according to claim 34, wherein said medium slide (16e) is spoon-shaped.

39. The dispenser according to claim 34, wherein said medium slide (16e) is insertable into said magazine chamber (30e).

40. The dispenser according to claim 34, wherein said medium slide (16e) is cam-controlled.

41. The dispenser according to claim 34, wherein said medium slide (16e) is mandrel-shaped.

42. The dispenser according to claim 34, wherein said medium slide (16e) is a guide on a basic body (8e) supporting a pump piston (25e).

43. The dispenser according to claim 33, wherein said refilling device has a magazine body (16d) having at least one chamber (30d) in a closed condition along two opposing sealing members (12d, 13d) which extend between a feed opening (71) of said magazine (69) and said feed path (20d).

44. The dispenser according to claim 33, wherein the medium contained in said magazine (69) is stress loaded by a piston (72).

45. The dispenser according to claim 33, wherein said feed opening (71) is constricted with respect to said magazine (69).

46. The dispenser according to claim 33, wherein said magazine body (16d) is substantially completely encapsulated within said dispenser.

47. The dispenser according to claim 1, wherein a separate chamber opener (50h) is provided for opening at least one of said magazine chamber (30h), means being provided for engaging said chamber opener (50h) on an opener end of said dispenser, said chamber opener (50h) providing a perforating needle (52h) mounted in spring-loaded manner on a plug body (82), a handle (5h) being provided in the vicinity of an end remote from said opener end, said handle (5h) laterally freely projecting on remote sides, a tappet (37h) axially projecting from said handle (5h) and having an operating handle (6h) displaceable for operating the secondary feed flow.

48. The dispenser according to claim 1, wherein at least one of said magazine chamber (30k) has a longitudinal extension and remote ends at least one of said magazine chamber (30k) being formed by at least one chamber casing providing at least one chamber space split transversely to said longitudinal extension between said remote ends, means being provided for opening and filling at least one of said magazine chamber (30k) in non-destructive manner.

49. The dispenser according to claim 34, wherein said medium slide (16e) is a guide on a casing part bearing a vibrator (75) for the medium when stored and a mounting support freely projecting ore a casing part with an actuating section (74).

50. The dispenser according to claim 48, wherein said chamber casing (22k) is positioned coaxially with the generator (4k).

51. The dispenser according to claim 48, wherein said chamber casing (22k) is received within said casing part.

52. The dispenser according to claim 48, wherein said chamber casing (22k) is integrally formed with a casing part for the generator (4k).

53. The dispenser according to claim 48, wherein a casing cover (13k) is provided with a discharge opening (11k) for the medium and an exterior operating handle (5k).

54. The dispenser according to claim 48, wherein opening devices (50k, 51k) are provided at opposite ones of said remote ends of said magazine chamber (30k).

55. The dispenser according to claim 54, wherein at least one of said two opening devices (50k, 51k) has at least one opening tool (48k) displaceably mounted against a spring tension, at least one of said opening tool (48k) being loaded by a return spring (27k) of at least one of said actuating means (3k) towards an abutted operational position.

56. A dispenser for dispensing media comprising:
a casing part (12n);
a magazine body (16n) providing at least one magazine chamber (30n) for receiving a dosage unit of the media, said magazine chamber (30n) having at least one magazine aperture (46n, 47n) for connecting said magazine chamber (30) to a discharge duct means (20), and
means in said casing part (12n) for receiving said magazine body (16n) in an inserted state when said magazine body (16n) is transferred from an initial state external to said casing part (12n) into said casing part (12n),
wherein in said initial state said magazine aperture (46n, 47n) is closed with at least one closure (45n), means (50n, 51n) being provided for opening said magazine aperture (46n, 47n) during transfer of said magazine body (16n) from said initial state to said inserted state, wherein said transfer occurs prior to media dispensing operations.

57. The dispenser according to claim 56, wherein said closure is provided by a closure body (45n) slideably engaging said magazine body (16n), said opening means (50n, 51n) being provided for operationally sliding said closure body (45n) into an opening position upon inserting said magazine chamber (30n) into said dispenser (1n).

* * * * *

UNITED STATES PATENT AND TRADEMARK OFFICE
CERTIFICATE OF CORRECTION

PATENT NO.  : 5,366,122

DATED       : November 22, 1994

INVENTOR(S) : Guentert, et al.

It is certified that error appears in the above-identified patent and that said Letters Patent is hereby corrected as shown below:

| | |
|---|---|
| Col. 2, line 44 | "mope" should be --more--. |
| Col. 3, line 54 | "one end" should be --one end by a cover--. |
| Col. 4, line 10 | "reception magazine" should be --reception or magazine--. |
| Col. 6, line 4 | "cap,like" should be --cap-like--. |
| Col. 7, line 5 | "ill" should be --in--. |
| Col. 8, line 34 | "magazine body" should be --magazine body 16--. |
| Col. 8, line 47 | "84" should be --54--. |
| Col. 8, line 63 | "coaxial" should be --coaxial to--. |
| Col. 10, line 20 | "sleeve" should be --sleeve 65,--. |
| Col. 11, line 5 | "through,open-" should be --through open--. |
| Col. 11, line 37 | "generator 46" should be --generator 4b--. |
| Col. 11, line 41 | "another accordingly" should be --another is accordingly--. |
| Col. 12, line 57 | "and-/or" should be --and/or--. |

UNITED STATES PATENT AND TRADEMARK OFFICE
CERTIFICATE OF CORRECTION

PATENT NO. : 5,366,122
DATED : November 22, 1994
INVENTOR(S) : Guentert, et al.

It is certified that error appears in the above-identified patent and that said Letters Patent is hereby corrected as shown below:

| | |
|---|---|
| Col. 14, line 60 | "48" should be --46--. |
| Col. 15, line 11 | "80" should be --60--. |
| Col. 16, line 41 | "58" should be --53--. |
| Col. 17, line 45 | "18" should be --13--. |
| Col. 17, line 61 | "forms inlet" should be --forms the inlet--. |
| Col. 18, line 9 | "sides blind" should be --sides to blind--. |
| Col. 19, line 23 | "in" should be --1n--. |
| Col. 21, line 20 | "ends (47)" should be --ends (46, 47)--. |
| Col. 22, line 14 | "generator" should be --generator (4a)--. |
| Col. 22, line 63 | "chamber" should be --chamber (30)--. |
| Col. 23, line 2 | "medium" should be --magazine--. |
| Col. 24, line 17 | "at least" should be --to at least--. |
| Col. 25, line 19 | "ore" should be --ove--. |

Signed and Sealed this

Second Day of May, 1995

Attest:

BRUCE LEHMAN

*Attesting Officer*       *Commissioner of Patents and Trademarks*